United States Patent [19]

Haas et al.

[11] 4,004,026

[45] Jan. 18, 1977

[54] DICARBOXYLIC ACIDS AND DERIVATIVES IN THE TREATMENT OF PAIN AND INFLAMMATION

[75] Inventors: Georges Haas, Oberwil; Erwin F. Jenny, Basel; Alberto Rossi, Oberwil, all of Switzerland

[73] Assignee: Ciba-Geigy Corporation, Ardsley, N.Y.

[22] Filed: Nov. 18, 1975

[21] Appl. No.: 632,926

Related U.S. Application Data

[62] Division of Ser. No. 389,105, Aug. 16, 1973, Pat. No. 3,940,434.

[30] Foreign Application Priority Data

Aug. 24, 1972 Switzerland .................... 12538/72

[52] U.S. Cl. .................................. 424/311; 424/317
[51] Int. Cl.² .................. A61K 31/19; A61K 31/22
[58] Field of Search .......................... 424/317, 311

*Primary Examiner*—Stanley J. Friedman
*Attorney, Agent, or Firm*—Joseph G. Kolodny; Theodore O. Groeger; John J. Maitner

[57] ABSTRACT

Benzocycloalkenderivatives substituted in 1-position by carboxyl and carboxyalkyl or two carboxyl groups, and further substituted in the benzene ring by cycloalkyl and optionally other substituents, their esters, amides and pharmaceutically acceptable salts have antiinflammatory and analgesic activity and can be used for the treatment of inflammatory conditions and pain in mammals; a representative embodiment is 1-methoxycarbonyl-5-cyclohexyl-6-chloro-1-indanecarboxylic acid.

8 Claims, No Drawings

DICARBOXYLIC ACIDS AND DERIVATIVES IN THE TREATMENT OF PAIN AND INFLAMMATION

This is a division, of application Ser. No. 389,105, filed Aug. 16, 1973 (now U.S. Pat. No. 3,940,434).

The invention relates to new dicarboxylic acid derivatives of the formula

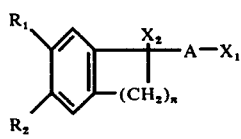

wherein A denotes a direct bond or a methylene group which is optionally substituted by a lower alkyl radical, one of the groups $R_1$ and $R_2$ denotes hydrogen, halogen, lower alkyl, lower alkanoyl, lower alkoxy, an optionally acylated hydroxyl or amino group, trifluoromethyl or nitro and the other denotes a saturated cycloaliphatic radical, $X_1$ and $X_2$ independently of one another denote free, esterified or amidised carboxyl groups and n denotes an integer from 1 to 3, as well as salts of these compounds, processes for their manufacture, intermediate products which arise in these processes, pharmaceutical preparations which contain these compounds, and their use.

The term "lower" which is used in the preceding and the following text in conjunction with organic radicals, groups or compounds denotes that organic radicals, groups or compounds thus described contain up to 7, preferably up to 4, carbon atoms.

A lower alkyl radical is, for example, a methyl, ethyl, n-propyl, isopropyl, n-butyl, isobutyl, sec.-butyl, tert.-butyl, n-pentyl, isopentyl, neopentyl, n-hexyl, isohexyl, n-heptyl or isoheptyl radical.

A group $R_1$ or $R_2$ as halogen is iodine, bromine, or preferably chlorine and fluorine; as lower alkyl it is, for example, one of the lower alkyl groups listed above, preferably methyl and ethyl; as lower alkanoyl it is formyl and acetyl, and also propionyl, butyryl, isobutyryl, valeryl, isovaleryl, hexanoyl and heptanoyl; as lower alkoxy it is methoxy and ethoxy, and also propoxy, isopropoxy, butoxy, isobutoxy, tert.-butoxy, pentoxy, isopentoxy, neopentoxy, hexoxy, isohexoxy and heptoxy; as an acylated hydroxyl or amino group it is a hydroxyl or amino group which is substituted by, for example, one of the abovementioned lower alkanoyl groups, preferably by formyl or acetyl, or by a benzoyl group which is optionally substituted, for example by halogen, nitro or methyl, preferably benzoyl.

A cycloaliphatic radical $R_1$ or $R_2$ is a lower alkylsubstituted or preferably unsubstituted cycloalkyl group with 4 to 8, preferably with 5 to 7, carbon atoms, such as the cyclopentyl, cyclohexyl and cycloheptyl group.

By esterified carboxyl groups $X_1$ and/or $X_2$ there are in particular understood those which are esterified with aliphatic or araliphatic alcohols, such as with lower alkanols which are optionally substituted, for example by one or more free or etherified hydroxyl groups, phenyl groups or pyridyl groups, for example with methanol, ethanol, propanols, butanols or glycerine of which the two hydroxyl groups which are not esterified with the carboxylic acid can be functionally modified, for example acetalised or ketalised with a lower alkanone, such as formaldehyde or acetone, and also with benzyl alcohol as well as with pyridine-methanols, for example 2- or 4-pyridine-methanol.

Amidised carboxyl groups $X_1$ and/or $X_2$ are unsubstituted, monosubstituted or disubstituted at the nitrogen. Substituents are, above all, hydrocarbon radicals, such as lower alkyl groups, especially those mentioned above, lower alkylene groups, for example the 1,4-butylene or 1,5-pentylene group, in which a —$CH_2$— group can be replaced by a hetero-atom, such as oxygen, or by an optionally lower alkylated imino group, such as, in particular, the methylimino group, and which together with the amide nitrogen can form a heterocyclic radical, such as the pyrrolidino, piperidino, morpholino, piperazino or 4-methylpiperazino group, the phenyl group and also the hydroxyl group, which forms, together with the carbamoyl radical, the hydroxamic acid grouping. Two carboxyl groups $X_1$ and $X_2$ can, especially if A in the formula I is a methylene group optionally substituted by a lower alkyl group, also be amidised with the same optionally substituted amine nitrogen atom and form, together with the quaternary ring carbon atom, a spirocyclically bonded imide grouping.

Salts can be manufactured in the usual manner from the acids which fall under the compounds according to the invention, for example from compounds of the formula I wherein at least one of the two groups $X_1$ and $X_2$ is a carboxyl group or hydroxamic acid group. Preferred salts are the pharmaceutically usable salts, such as metal salts, for example alkali metal, alkaline earth metal or earth metal salts, such as lithium, sodium, potassium, magnesium, calcium and aluminium salts, ammonium salts and salts with organic bases, such as lower alkylamines which are optionally substituted, for example by hydroxyl or phenyl, such as ethylamine, 2-aminoethanol, benzylamine, diethanolamine, 2-dimethylaminoethanol, trimethylamine or triethylamine, and lower alkyleneamines wherein a carbon atom can optionally be replaced by a hetero-atom, such as oxygen, such as pyrrolidine, piperidine and morpholine.

Salts can also be manufactured from the bases which fall under the compounds according to the invention, for example from compounds of the formula I or IIa', wherein $X_1$ or $X_2$ represent carboxyl groups which are esterified by a basic alcohol, for example a pyridine-methanol, or are amidised by an amine containing two basic nitrogen atoms, for example 4-methylpiperazine. Such compounds can form addition salts with acids. Acids suitable for salt formation are, in particular, pharmaceutically usable acids, for example inorganic acids, such as hydrogen halide acids, for example hydrochloric acid, acids of sulphur, such as sulphuric acid, acids of phosphorus, such as phosphoric acid, or organic acids, such as methanesulphonic acid or ethanesulphonic acid, $\beta$-hydroxyethanesulphonic acid, acetic acid, malonic acid, citric acid, lactic acid, oxalic acid, succinic acid, fumaric acid, maleic acid, benzoic acid, salicylic acid, phenylacetic acid, mandelic acid, embonic acid and the like.

The compounds according to the invention possess valuable pharmacological properties, especially antiinflammatory and analgesic activity, coupled with an advantageous therapeutic index. The anti-inflammatory activity manifests itself, for example, in the kaolin oedema test on the paws of rats, according to L. Riesterer and R. Jaques, Helv. physiol. pharmakol. Acta 25, 156 (1967), in which the compounds according to the invention have a detectable action on peroral administration of about 3 to 100 mg/kg.

The analgesic effects can be demonstrated, for example, with the aid of the writhing test on mice, such as according to the method developed by Siegmund et al., Proc. Soc. Exptl. Biol. Med., Volume 95, page 729 (1957), at oral doses of about 30 to about 100 mg/kg.

The compounds of the present invention can therefore be used as non-narcotic analgesics and in particular as anti-inflammatory agents, above all for the treatment of arthritic symptoms. They can also be used as intermediate products in the manufacture of other pharmacologically active, valuable compounds.

Preferred compounds of the invention are those of the formula I, wherein one of the groups $R_1$ and $R_2$ denotes hydrogen, fluorine, chlorine, methyl, ethyl, methoxy, ethoxy or trifluoromethyl and the other denotes a cycloalkyl group with 4 to 8 carbon atoms, the groups $X_1$ and $X_2$ independently of one another denote a carboxyl group, a lower alkoxycarbonyl group or an unsubstituted carbamoyl group and A denotes a direct bond or a methylene group, as well as pharmaceutically tolerated salts of the free carboxylic acids.

Particularly preferred compounds of the invention are those of the formula I, wherein the group $R_1$ is hydrogen or chlorine and $R_2$ is cyclopentyl, cyclohexyl or cycloheptyl, $X_1$ denotes a free carboxyl group, $X_2$ denotes a lower alkoxycarbonyl group, A denotes a direct bond and n denotes 2, as well as pharmaceutically tolerated salts of these compounds.

In particular, the following compounds are preferred: 1-methoxycarbonyl-5-cyclohexyl-6-chloro-1-indanecarboxylic acid, 1-butoxycarbonyl-5-cyclohexyl-6-chloro-1-indanecarboxylic acid, 1-methoxycarbonyl-5-cycloheptyl-6-chloro-1-indanecarboxylic acid, 1-propoxycarbonyl-5-cycloheptyl-6-chloro-1-indanecarboxylic acid, 1-butoxycarbonyl-5-cycloheptyl-6-chloro-1-indanecarboxylic acid and 1-methoxycarbonyl-5-cyclohexyl-1-indanecarboxylic acid.

The compounds of the present invention can be obtained according to methods which are in themselves known. Thus they can be formed, for example, from a compound of the formula

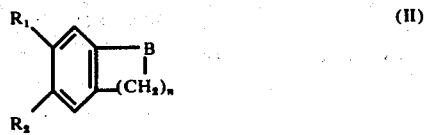

(II)

wherein B denotes a radical which can be converted into a group of the formula $=C(X_2)-A-X_1$ (Ia), by carrying out this conversion and, if desired, converting a resulting compound according to the invention into another compound of the invention, within the defined scope.

Thus it is possible to condense a compound of the formula

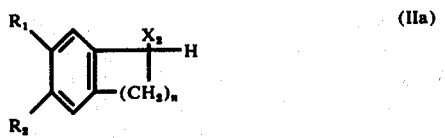

(IIa)

which falls under the general formula II, with a reactive functional derivative of a hydroxy compound of the formula HO—A—$X_1$ (III) to give a compound of the formula I and, if desired, to carry out further reactions within the scope defined.

Reactive functional derivatives of compounds of the formula III, wherein A is a direct bond, are derivatives of carbonic acid, such as anhydrides, esters or amides thereof. These are, above all, carbon dioxide, and also esters, for example di-lower alkyl esters, such as diethyl esters, of carbonic acid, halogenoformic acid derivatives, such as chloroformic acid lower alkyl esters, such as chloroformic acid methyl esters, or amides of chloroformic acid, such as chloroformic acid dimethylamide.

Reactive functional derivatives of compounds of the formula III, wherein A is an optionally mono-lower alkylated methylene group, are above all reactive esters of α-hydroxy-lower alkane carboxylic acid derivatives. A reactive ester contains, for example, a hydroxyl group esterified with a strong acid, such as with a hydrogen halide acid, for example with hydrochloric acid, hydrobromic acid or hydriodic acid. Examples of reactive esters of compounds of the formula III are α-bromo-lower alkane carboxylic acids, such as bromoacetic acid, their lower alkyl esters, such as bromoacetic acid methyl ester, or their amides, such as lower alkylamides, for example bromoacetic acid dimethylamide.

The condensation is advantageously carried out in the presence of a base, for example of an alkali metal amide, hydride or lower alkanolate, such as sodium amide, lithium hydride or potassium tert.-butoxide, of a quaternary ammonium base which is quaternised, for example by lower alkyl or benzyl, for example benzyl-trimethylammonium methoxide, or preferably of an alkali metal di-lower alkylamide, such as lithium diisopropylamide, in a solvent. Examples of solvents which can be used are lower alkanols, such as methanol or tert.-butanol, ether-like liquids, such as di-lower alkyl ethers, for example diethyl ether, cyclic ethers, for example tetrahydrofurane, and liquid amides, such as di-lower alkylamides of lower alkanoic acids or of phosphoric acid, for example dimethylformamide or hexamethylphosphoric acid triamide.

According to another process variant, the compounds according to the invention can be manufactured from a compound falling under the general formula II, of the formula

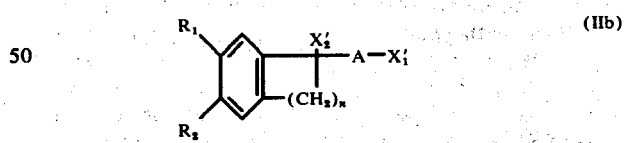

(IIb)

in which one of the groups $X'_1$ and $X'_2$ denotes a free, esterified or amidised carboxyl group or a group which can be converted into such a group and the other denotes a group which can be converted into a free, esterified or amidised carboxyl group, by carrying out this conversion and, if desired converting a resulting compound according to the invention into another compound of the invention within the defined scope. Examples of radicals which can be converted into free, esterified or amidised carboxyl groups are radicals which can be hydrolysed or alcoholysed to such groups, such as, for example, the nitrile group. Further examples of hydrolysable, alcoholysable or amidisable radicals are acyloxycarbonyl groups, for example lower alkanoyloxycarbonyl groups, such as the acetoxycarbonyl group or the benzoloxycarbonyl group, or halogenocarbonyl groups, such as, in particular, the chlorocarbonyl group.

The hydrolysis of the nitrile group to the free carboxyl group can be carried out in an acid medium, for example in the presence of a strong inorganic acid, such as hydrochloric acid or sulphuric acid, in water or in a mixture of water and a solvent miscible therewith, such as a lower alkanoic acid, for example acetic acid, or an ether-like liquid, such as dioxane. Preferably, however, the hydrolysis is carried out in an alkaline medium, for example in the presence of a strong base, such as an alkali metal hydroxide or alkaline earth metal hydroxide, such as sodium hydroxide or calcium hydroxide, or of an alkali metal carbonate, for example potassium carbonate. Advantageously, a solvent is used for this reaction, for example water, a lower alkanol, such as ethanol, a lower alkanediol, such as ethylene glycol, or a mixture of water and a solvent miscible therewith, such as dioxane.

The hydrolysis of the nitrile group to the corresponding carboxyl group takes place via the carbamoyl group as an intermediate step; the latter can be isolated if desired. The hydrolysis to the carbamoyl group can be carried out, for example, in 96% strength sulphuric acid at approximately room temperature, or in a basic medium, advantageously in the presence of a hydroperoxide, for example in hydrogen peroxide solution containing sodium hydroxide.

The alcoholysis of the nitrile group leads to the esterified carboxyl group via an etherified hydroxyformimidoyl group, for example a hydroxyformimidoyl group which is lower-alkylated at the oxygen. The reaction is advantageously carried out in the presence of a hydrogen halide acid in the alcohol used for the esterification, such as a lower alkanol, if desired in the presence of a diluent, such as a di-lower alkyl ether, for example diethyl ether. The etherified hydroxyformimidoyl group, which can optionally be present in the form of a salt with a strong acid, such as hydrochloric acid, can be isolated if desired and be hydrolysed, analogously to the hydrolysis of the nitrile group, to the corresponding carboxyl group. This reaction takes place via the corresponding esterified carboxyl group, which can be isolated if desired.

An acyloxycarbonyl group or halogenocarbonyl group can be converted into a free carboxyl group by reaction with water, optionally in the presence of a base, for example of an alkali metal or alkaline earth metal hydroxide, carbonate or bicarbonate, for example sodium hydroxide, sodium carbonate or sodium bicarbonate, or can be converted into an ester by reaction with an alcohol, or can be converted into an amidised carboxyl group by reaction with ammonia or a primary or secondary amine.

According to a further variant of the process, the compounds according to the invention can be manufactured by oxidising a compound falling under the general formula II, of the formula

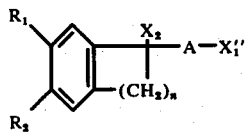

(IIc)

wherein $X''_1$ denotes a hydroxymethyl or acyl group and, if desired, converting a resulting compound of the invention into another such compound within the defined scope.

By acyl groups there are understood the acyl groups initially listed, especially lower alkanoyl, such as formyl and acetyl, and also benzoyl. The oxidation of the hydroxymethyl group and of the formyl group can preferably be carried out with an oxidising agent, such as with oxygen, with a metal compound of a higher oxidation level, for example with a compound of 6-valent chromium, such as chromic acid, or of 7-valent or 4-valent manganese, such as potassium permanganate and manganese dioxide, with silver oxide, with nitric acid, with a hydroperoxide, such as hydrogen peroxide, or with a hypohalite, such as sodium hypochlorite. The hypohalites are particularly suitable for oxidising the acetyl group, a trihalogenoacetyl group being produced as an intermediate product, which is split to the carboxyl group under the reaction conditions. The oxidation is advantageously carried out in a solvent which is inert under the conditions used, for example in water, in a lower alkanoic acid, such as acetic acid, in a di-lower alkyl ketone, such as acetone, in an ether-like solvent, such as dioxane, or in an optionally chlorinated hydrocarbon, such as benzene or carbon tetrachloride.

The oxidation of the hydroxymethyl group to the carboxyl group can be carried out in one or two steps depending on the nature and amount of the oxidising agent used. In the latter case, the compound of the formula (IIc), wherein $X''_1$ denotes the formyl group, which arises as an intermediate step, can either be isolated or directly oxidised further to the desired compound of the formula (I), wherein $X_1$ denotes the carboxyl group, by adding a further amount of a suitable oxidising agent.

To oxidise the acyl group, such as the lower alkanoyl group or benzoyl group, this group is preferably first oximised. The oximation can be carried out in the usual manner, for example by reaction with hydroxylamine or with a salt thereof, such as the hydrochloride thereof, preferably in a solvent, such as water or a lower alkanol, such as ethanol. Thereafter, the oxime is treated by the Beckmann method with a strong acid, for example polyphosphoric acid or sulphuric acid, or a Lewis acid, such as phosphorus trichloride or titanium tetrachloride, whereupon the acyl group undergoes rearrangement to a carbamoyl group, that is to say is oxidised intramolecularly. It is also possible first to convert the oxime into a sulphonic acid ester by means of a sulphonyl halide, for example by means of an aliphatic or aromatic sulphonyl chloride, such as methanesulphonyl chloride, benzenesulphonyl chloride or toluenesulphonyl chloride, preferably in the presence of a base, such as pyridine, and this sulphonic acid ester can be rearranged spontaneously or by warming. The resulting carbamoyl group is monosubstituted at the nitrogen, for example by lower alkyl or phenyl, in accordance with the oximised carbonyl group present in the starting material. Depending on the reaction conditions, the Beckmann rearrangement of an oximised formyl group gives the carboxyl group, the unsubstituted carbamoyl group or the nitrile group.

A hydroxymethyl group is preferably oxidised to the formyl group with a mixture of N-chlorosuccinimide and dimethylsulphoxide, using an inert hydrocarbon, such as toluene, as the solvent. A formyl group is preferably oxidised to the carboxyl group with silver oxide, for example in tetrahydrofurane as the solvent.

According to a further process variant, compounds of the formula I, wherein A denotes a methylene group which is optionally substituted by a lower alkyl group, can be manufactured by replacing Y by hydrogen in a compound falling under the general formula II, of the formula

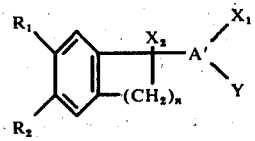

(IId)

in which A' is a methine group which is optionally substituted by a lower alkyl group and Y is a group replaceable by hydrogen and, if desired, converting the resulting compound into another compound within the defined scope.

An example of a group Y is the carboxyl group which can be replaced by hydrogen through decarboxylation. To carry out the decarboxylation, a starting material is warmed in the presence or absence of a solvent and/or of a catalyst. The solvents used are, for example, water, alcohols, such as lower alkanols, for example ethanol, lower alkanediols, such as ethylene glycol, higher-boiling ether-like solvents, such as dibutyl ether, dioxane and diphenyl ether, or, preferably, liquid nitrogen bases, such as pyridine, quinoline or collidines. Examples of catalysts which can be used are copper or copper salts, such as copper (I) chloride.

Further groups Y are the acyl groups, such as lower alkanoyl groups, for example the acetyl group, which can be replaced by hydrogen, especially if $X_1$ and $X_2$ are esterified carboxyl groups, by treatment with a strong base, for example with an alkali metal lower alkanolate, such as sodium ethylate, preferably in a solvent, such as in a lower alkanol, for example ethanol.

Resulting compounds of the invention can be converted into other compounds according to the invention in the usual manner within the defined scope. Thus it is possible, in compounds of the formula I in which one or both groups $X_1$ and $X_2$ are a free carboxyl group, to convert one or both of these groups into esterified or amidised carboxyl groups. For example, an esterification can be carried out by reacting the carboxylic acid with a suitable alcohol, such as a lower alkanol, for example methanol, preferably in the presence of an acid catalyst, such as a Lewis acid, for example boron trifluoride, or of a proton acid, for example hydrochloric acid, sulphuric acid or toluenesulphonic acid, and also of an agent which splits off water, such as a carbodiimide, for example dicyclohexylcarbodiimide. In this method, the reaction is advantageously carried out using, as the solvent, an excess of the alcohol employed. A further direct method of esterification is the reaction of the acid, or of one of its salts, such as the sodium salt, with a reactive functional derivative, for example a reactive ester, of a suitable alcohol, such as of a lower alkanol, for example with a halide, such as an iodide or bromide, for example with methyl iodide, or with a suitable diazo compound, such as a diazo-lower alkane, for example diazomethane. The reaction is preferably carried out in a solvent, for example in an ether-like liquid, such as a di-lower alkyl ether, for example diethyl ether, or in a cyclic ether, such as tetrahydrofurane.

However, the esterification can also be carried out indirectly via a reactive functional derivative of the carboxylic acid falling under the formula I, such as an anhydride, for example a mixed anhydride with a hydrogen halide acid, such as hydrochloric acid. In this method, a carboxylic acid falling under the formula I is first reacted, for example with an acid anhydride, such as with an acid halide, for example of phosphorous acid or sulphurous acid, for example with phosphorus trichloride or thionyl chloride, and the resulting reactive derivative, for example, chloride, of the carboxylic acid is then allowed to react with a suitable alcohol, such as a lower alkanol, if desired in the presence of a base, for example of a nitrogen-containing heterocyclic compound, such as pyridine, or of an alkali metal carbonate, such as potassium carbonate. The reaction is preferably carried out in a solvent, for example in an excess of the alcohol used, or in an ether-like solvent, such as diethyl ether.

The amidation of a free carboxylic acid can also be carried out direct, for example by treating one of the salts which it forms with ammonia or with a suitable primary or secondary amine, such as a mono- or di-lower alkylamine, pyrrolidine, piperidine, morpholine, aniline or hydroxylamine, at elevated temperature and/or in the presence of an agent which splits off water, for example of a Lewis acid, such as silicon tetrachloride. Advantageously, however, the reaction is carried out indirectly. For example, a reactive functional derivative (manufactured as above) of the carboxylic acid falling under the formula I, such as a chloride, is reacted with one of the abovementioned amines or ammonia. The reaction is advantageously carried out in the presence of a base, for example of an excess of the amine required for the reaction, in a solvent, for example in water, in a lower alkanol, such as ethanol, or in an ether-like solvent, such as a di-lower alkyl ether, for example diethyl ether.

In compounds of the formula I, wherein $X_1$ and/or $X_2$ are esterified or amidised carboxyl groups, one or both of these groups can be hydrolysed to free carboxyl groups in the usual manner. The hydrolysis can be carried out in an acid medium, for example in the presence of a strong inorganic acid, such as hydrochloric acid or sulphuric acid, in water or in a mixture of water and a solvent miscible therewith, such as a lower alkanoic acid, for example acetic acid, or an ether-like liquid, such as dioxane. Preferably, however, the hydrolysis is carried out in an alkaline medium, for example in the presence of a strong base, such as an alkali metal hydroxide or alkaline earth metal hydroxide, for example sodium hydroxide or potassium hydroxide, or of an alkali metal carbonate, for example potassium carbonate. For this, a solvent is advantageously used, for example water, a lower alkanol, such as ethanol, a lower alkanediol, such as ethylene glycol, or a mixture of water and a solvent miscible therewith, such as dioxane.

In compounds of the formula I, wherein one or both groups $X_1$ and $X_2$ denote esterified or amidised carboxyl groups, these can be converted into esterified or amidised carboxyl groups different therefrom.

Thus, an esterified carboxyl group can be converted into a carbamoyl group in the usual manner by reaction with ammonia or one of the abovementioned suitable amines. The reaction can be carried out in the presence or absence of a solvent, for example of a lower alkanol, such as ethanol, or of an ether-like solvent, such as dioxane. An esterified carboxyl group can also be trans-esterified with an alcohol different from the alcohol which it contains, in the usual manner, preferably in the presence of an acid, such as a Lewis acid, for example boron trifluoride, or a proton acid, such as hydrochloric acid, and also in the presence of a base, for example of an alkali metal alcoholate derived from the alcohol used for the trans-esterification. The trans-esterification is preferably carried out in a solvent, for example in an excess of the alcohol used for the trans-esterification. It is also possible to cary out conversions within the alcohol radical of the esterified carboxyl group; thus, for example, in a glycerine monoester the free hydroxyl groups can be functionally modified, for example acetalised or ketalised with a lower alkanone, or in a glycerine monoester of which the free hydroxyl groups are acetalised or ketalised, these can be split hydrolytically.

An amidised carboxyl group can be converted into an esterified carboxyl group via the hydroxyformimidoyl group which is correspondingly etherified, for example lower-alkylated at the oxygen.

An etherified hydroxyformimidoyl group can be obtained if a carbamoyl group is treated with an oxygen-alkylating agent, for example with an oxonium salt, such as a tri-lower alkyloxonium salt, for example with triethyloxonium fluoborate, in a solvent, such as in an ether-like liquid, for example diethyl ether. On careful hydrolysis, for example in water, optionally in the presence of a diluent, for example of a water-soluble organic solvent, such as dioxane, this group yields the esterified carboxyl group.

If the two groups $X_1$ and $X_2$ in a compound of the formula I are identical, the conversions described above can be carried out on free or functionally modified carboxyl groups in such a way that both groups are converted; if desired they can however be conducted in such a way, for example by using equivalent amounts of the reagents and/or interrupting the reaction at a suitable point in time, that only one of the groups $X_1$ or $X_2$ is reacted.

In resulting compounds of the formula I, wherein A is unsubstituted methylene, the latter can be substituted by a lower alkyl group in the usual manner. The alkylation can be effected, for example, by treatment with a reactive ester of a lower alkanol, for example with a halide, such as an iodide or bromide, for example with methyl iodide, preferably in the presence of a base. As the base it is possible to use alkali metal hydrides, amides or lower alkanolates, for example sodium hydride, lithium amide or potassium tert.-butoxide, quaternary ammonium bases which can be quaternised by, for example, lower alkyl or benzyl, such as benzyl-trimethylammonium methoxide, or, preferably, an alkali metal lower alkylamide, such as lithium diisopropylamide. The alkylation is preferably carried out in a solvent, for example in a lower alkanol, such as tert.-butanol, in an ether-like solvent, such as a di-lower alkyl ether, for example diethyl ether or a cyclic ether, such as tetrahydrofurane, or in a liquid amide, for example in a di-lower alkylamide of a lower alkanoic acid or of phosphoric acid, such as dimethylformamide or hexamethylphosphoric acid triamide.

Compounds of the formula I, wherein A denotes the direct bond, can be converted into compounds of the formula I, wherein A is a methylene group which is optionally substituted by a lower alkyl group. For example, a compound of the formula I, wherein A is a direct bond and one of the groups $X_1$ and $X_2$ is a free carboxyl group and the other is an amidised or, preferably, esterified carboxyl group, is first reacted in the manner described above to give a reactive functional derivative at the free carboxyl group, such as an anhydride, for example with a strong acid, such as a hydrogen halide acid, for example reacted to give the chloride, and the derivative is allowed to react with a diazo-lower alkane. The resulting compound, wherein the free carboxyl group is replaced by a radical of the formula $-CO-A''=N \equiv N$, is then reacted wih water, an alcohol, ammonia or an amine.

The above reaction is carried out according to the Arndt-Eistert and Wolff method, preferably in the presence of a noble metal or of a nobel metal salt as the catalyst, for example in the presence of copper or platinum or preferably of a silver salt, such as silver nitrate, or silver oxide, or of a complex salt thereof with sodium thiosulphate. The reaction is preferably carried out in the presence of a solvent, advantageously in the excess of water, alcohol or amine required for the solvolysis, and also in the presence of an inert diluent, such as an ether-like solvent, for example dioxane, a ketone, such as a lower alkyl ketone, for example acetone, a carboxylic acid, such as a lower alkanoic acid, for example acetic acid, or an amide, such as a dilower alkylamide, of a lower alkanoic acid, for example dimethylformamide or dimethylacetamide.

In resulting compounds, substituents can be introduced, modified or removed within the defined scope.

In resulting compounds in which $R_1$ or $R_2$ is hydrogen, the hydrogen can be replaced. Substituents which can be introduced directly are, for example, the nitro group, lower alkanoyl groups and halogen atoms. They are introduced in the customary manner, for example by nitration in the case of the nitro group. The nitration is carried out in a manner which is in itself known, for example by treatment with a mixture of concentrated sulphuric acid and concentrated nitric acid, or with a mixed anhydride of nitric acid and a carboxylic acid, for example a lower alkanoic acid, such as acetic acid.

Lower alkanoyl groups can be introduced by Friedel-Crafts acylation. Acylation is carried out, for example, with an anhydride, for example a halide, such as a chloride, of a lower alkanecarboxylic acid, preferably in the presence of a Lewis acid, such as aluminium chloride, in a solvent, such as carbon disulphide, methylene chloride or nitrobenzene.

Halogen atoms are introduced, for example, directly, as by reaction with elementary halogen or halogen donors, appropriately in the presence of catalysts, for example iron-(III) chloride.

In resulting compounds which contain a radical $R_1$ or $R_2$ which differs from hydrogen, this radical can be converted or split off.

In resulting compounds which contain a free hydroxyl group $R_1$ or $R_2$, this group can be etherified. The etherification is carried out in the usual manner, for example by reaction with a reactive ester of a lower alkanol, preferably in the presence of a strong base, or with a diazo-lower alkane, such as diazomethane.

In resulting compounds which possess an alkoxy radical as the group $R_1$ or $R_2$, this radical can be converted into the free hydroxyl group in the usual manner. This conversion is carried out, for example, by hydrolysis, above all by means of strong acids, such as hydriodic acid or hydrobromic acid, and optionally in the presence of light metal halides, such as aluminium bromide or boron bromide, or with pyridine hydrochloride or aluminium chloride in pyridine.

In resulting compounds which contain a nitro group, the latter can be reduced to an amino group, for example with one of the customary reducing agents, for example a metal and acid, such as iron and hydrochloric acid, or catalytically, for example with hydrogen and a transition metal catalyst, such as a palladium catalyst or nickel catalyst.

In resulting compounds which contain a free hydroxyl group or amino group on the aromatic ring, this group can be acylated. The acylation takes place in the usual manner, especially with reactive functional derivatives of the acids in question, preferably acid halides or acid anhydrides, appropriately in the presence of acid-binding agents, for example those mentioned. Conversely it is also possible to split off the acyl radicals in resulting compounds which carry acylamino groups or acyloxy groups on the benzene ring. The splitting off is effected in the usual manner, for example as indicated above for the hydrolysis of carbamoyl groups or ester groups $X_1$ and $X_2$.

In resulting compounds which possess an amino group as the radical $R_1$ or $R_2$, this group can be replaced by a hydroxyl group or alkoxy group, a halogen atom or a hydrogen atom. The replacement is carried out in the usual manner, especially by diazotisation, for example with nitrous acid, and subsequent introduction of the desired radical according to the customary methods. A hydroxyl group is introduced, for example, by warming an aqueous solution of a diazonium salt. The introduction of an alkoxy radical is preferably achieved by boiling the diazonium salt with the appropriate alcohol. The introduction of a halogen atom is effected, for example, by treating a diazonium salt with copper (I) halide according to the Sandmeyer method or by treating the appropriate diazonium halide with copper powder according to the Gattermann method. To introduce a hydrogen atom, the diazonium salt is advantageously reduced with alkali metal stannite.

The reactions mentioned above or subsequently which serve for the manufacture of the starting substances can be carried out in the usual manner, in the presence or absence of diluents, condensation agents and/or catalytic agents, at room temperature, lowered or elevated temperature, optionally in a closed vessel and/or under an inert gas atmosphere. The conversions of end products into end products can furthermore be carried out in optional sequence.

Depending on the process conditions and starting substances, the end products are obtained in the free form or in the form of their salts, which is also included in the invention. Resulting free compounds with acid groups, such as carboxylic acids hydroxamic acids, can be converted in the usual manner, for example by reaction with appropriate basic agents, into the salts with bases, above all into therapeutically usable salts with bases, for example with organic amines, or into metal salts. The free compounds can be liberated from the salts in the usual manner, for example by reaction with acid agents.

Resulting free compounds having a basic group can be converted into addition salts with acids, especially with the pharmaceutically tolerated acids mentioned, in the usual manner, and from these salts the bases can again be liberated in the usual manner by treatment with a stronger base.

These or other salts can also be used for the purification of the new compounds, for example by converting the free compounds into their salts, isolating these and reconverting them into the free compounds. Because of the close relationships between the new compounds in the free form and in the form of their salts, the free compounds are where appropriate also to be understood to include the corresponding salts, in respect of general sense and intended use, in the preceding and following text.

The new compounds can, depending on the choice of the starting substances and working methods and depending on the number of the asymmetrical carbon atoms, be in the form of optical antipodes, racemates or isomer mixtures (racemate mixtures).

Resulting isomer mixtures (racemate mixtures) can be separated in a known manner into the stereoisomeric (diastereomeric), pure racemates on the basis of the physico-chemical differences of the constituents, for example by chromatography and/or fractional crystallisation.

Resulting racemates can be resolved into the diastereomers according to known methods, for example by recrystallisation from an optically active solvent, with the aid of micro-organisms or by reaction with an optically active acid or base which forms salts with the racemic compound and separation of the salts obtained in this manner, for example by virtue of their different solubilities, and the antipodes can be liberated from the diastereomers by treatment with suitable agents. Preferred optically active bases are, for example, brucine, strychnine, morphine or $\alpha$-phenylethylamine or their quaternary ammonium bases. Advantageously, the more active and/or less toxic of the two antipodes is isolated.

However, it is also possible to manufacture pure isomers, racemates or optical antipodes by starting from the corresponding starting substances in the form of their pure isomers, racemates or optical antipodes.

The invention also relates to those embodiments of the process according to which a compound obtainable as an intermediate product at any stage of the process is used as the starting material and the missing process steps are carried out, or in which a starting substance is formed under the reaction conditions or in which a reactant is present in the form of its salt, if relevant.

Appropriately, those starting substances are used for carrying out the reactions according to the invention which lead to the initially particularly mentioned groups of end products and especially to the end products which have been particularly described or singled out.

The starting substances are known or can, if they are new, be manufactured according to methods which are in themselves known.

A starting compound of the formula IIa can be manufactured, for example, if in a compound of the formula

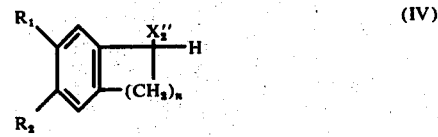

(IV)

wherein $X''_2$ denotes a radical which can be converted into an optionally esterified or amidised carboxyl group, this conversion is carried out and, if desired, a resulting compound of the formula IIa is converted into another such compound, within the defined scope.

$X''_2$ is, for example, a group, such as a nitrile group, which can be hydrolysed or alcoholysed to a free, esterified or amidised carboxyl group. The hydrolysis or alcoholysis can be carried out analogously to the conversion of compounds of the formula IIb, as described above.

$X''_2$ can also be a group which can be oxidised to a carboxyl group, such as hydroxymethyl or acyl, for example lower alkanoyl, such as formyl or acetyl, or benzoyl. The oxidation is carried out analogously to the oxidation of compounds of the formula IIc.

$X''$ can however also be a suitable metal atom, for example lithium or sodium, or the group of the formula —Mg—Hal, wherein Hal denotes a halogen atom, such as chlorine, bromine or iodine. Such a group $X''$ can be converted into a free carboxyl group or a carboxyl group modified as indicated, for example by reaction with a suitable derivative of carbonic acid. As such derivatives there should in particular be mentioned carbon dioxide, but also esters or half-esters of carbonic acid, especially lower alkyl esters, for example diethyl carbonate, or carbonic acid halide esters, that is to say halogenoformic acid esters, such as chloroformic acid lower alkyl esters, for example chloroformic acid ethyl esters. The reaction is carried out in the usual manner, preferably in an inert solvent, such as an ether, for example diethyl ether or dibutyl ether or tetrahydrofurane.

According to a further process variant, compounds of the formula IIa are obtained if, in a compound of the formula

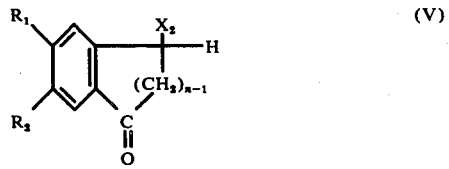

the carbonyl group is reduced to the methylene group and, if desired, a resulting compound is converted into another within the defined scope.

The reduction of the carbonyl group can be carried out directly, for example with hydrazine, advantageously in a high-boiling solvent, such as ethylene glycol, in the presence of a base, such as potassium hydroxide or sodium hydroxide, according to the Wolff-Kishner method. According to another variant, the carbonyl group is reduced according to the Clemmensen method with amalgamated zinc and hydrochloric acid in water, if desired in the presence of an inert solvent, for example of a hydrocarbon, such as toluene. However, another possible procedure is first to reduce the carbonyl group to a carbinol. This reduction can be carried out, for example, with a complex hydride, such as an alkali metal borohydride or alkali metal aluminiumhydride, for example with sodium borohydride, advantageously in water or in a lower alkanol. The resulting carbinol compound can be converted into an unsaturated compound by splitting off water, for example with an agent which splits off water, such as a strong acid, for example sulphuric acid or phosphoric acid, and the unsaturated compound is then converted into a compound of the formula IIa by means of hydrogen which is activated catalytically, for example with a transition metal catalyst, such as a palladium catalyst, platinum catalyst or nickel catalyst.

The carbinol can also be converted into an activated ester thereof, for example into a halide, such as a chloride, or a sulphonic acid ester, such as a toluenesulphonic acid ester. The conversion is carried out, for example, by treatment with a halide, such as a chloride, of sulphurous acid or phosphorous acid, or with a sulphonic acid chloride, such as toluenesulphonic acid chloride. This ester can also yield a compound of the formula IIa by reduction, for example with catalytically activated hydrogen or with one of the abovementioned complex hydrides.

The conversions within the defined scope, for example within the optionally esterified or amidised carboxyl group or within the substituents $R_1$ and $R_2$, can be carried out analogously to the corresponding conversions of the end products of the formula I.

The compounds of the formula

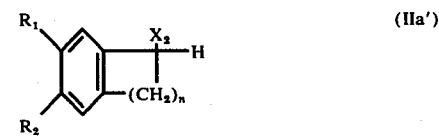

which falls under the general formula IIa, wherein $R_1$, $R_2$, $X_2$ and n have the meaning indicated under the formula I, with the proviso that if $R_2$ denotes cyclopentyl or cyclohexyl, n is 1, as well as salts thereof, are new compounds and also form a subject of the present invention. They possess valuable pharmacological, especially anti-inflammatory and analgesic, activity, which can be demonstrated according to the methods described initially. Because of this activity, the compounds of the formula IIa' can be used as agents having an analgesic action and especially an anti-inflammatory action, above all for the treatment of arthritic symptoms.

For example, the compounds of the formula IIa' are effective in the kaolin oedema test at about 3–100 mg/kg and in the writhing test at about 30–100 mg/kg.

Preferred compounds of the formula IIa' are those in which n is 1 or 2, one of the groups $R_1$ and $R_2$ is hydrogen or halogen, especially chlorine and the other is cyclopentyl, cyclohexyl or especially cycloheptyl, with the proviso that if $R_2$ denotes cyclopentyl or cyclohexyl, n is 1, and $X_2$ denotes a free carboxyl group or a carboxyl group esterified with a lower alkanol, especially butanol, or a pyridinemethanol, especially 4-pyridinemethanol, or denotes the carbamoyl group, and pharmaceutically tolerated salts of these compounds.

The following are particularly preferred compounds: 5-cycloheptyl-6-chloro-1-indanecarboxylic acid, 5-chloro-6-cyclohexyl-1-indanecarboxylic acid, 4-cyclohexyl-1-benzocyclobutenecarboxylic acid, 5-cyclohexyl-1-benzocyclobutenecarboxylic acid, 5-cycloheptyl-6-chloro-1-indanecarboxylic acid butyl ester, 5-cycloheptyl-6-chloro-1-indanecarboxylic acid 4-pyridinemethyl ester and 5-cycloheptyl-6-chloro-1-indanecarboxylic acid amide.

The starting substances of the formula V are known or can be obtained analogously to known compounds.

Compounds of the formula IV, wherein n is 2 or 3 can be obtained, for example, according to known methods from compounds of the formula

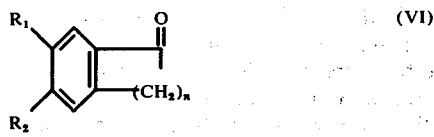

wherein n is 2 or 3, (which are obtainable, in turn, by decarboxylation of compounds of the formula V with $R_1$ and $R_2$ interchanged). For example, a compound of the formula VI is condensed with methoxymethyl-triphenylphosphonium bromide in the presence of a base, such as sodium hydride, and the enol-ether obtained is split, for example with a strong acid, such as perchloric acid, to give a compound of the formula IV, wherein $X''_2$ is the aldehyde group. The aldehyde group can, if desired, be reduced to the hydroxymethyl group, for example with a complex hydride of boron or of aluminium, for example with sodium hydride. The carbonyl compound of the formula VI can also be condensed with hydrogen cyanide or a salt thereof, such as potassium cyanide, to give a cyanohydrin which, after splitting off water and hydrogenating the resulting double bond in a manner which is in itself known, yields the compound of the formula IV, wherein $X''_2$ is the nitrile group and n is 2 or 3.

Compounds of the formula IV, in which $n = 1$, for example the 1-cyano-benzocyclobutenes which carry a cycloaliphatic hydrocarbon radical in the 4- or 5-position can be manufactured, for example, by starting from a correspondingly substituted m-halogenophenylacetic acid, in which halogen preferably denotes fluorine, chlorine or bromine, lengthening the aliphatic chain by one C atom by esterification, reduction to the alcohol and conversion into the chloride and cyanide, and reacting the β-(m-halogenophenyl)-propionitrile formed with agents which split off hydrogen halide, for example an alkali metal amide, such as potassium amide, in liquid ammonia. In doing so, a dehydrobenzene derivative is formed as an intermediate, with elimination of halogen, and from this derivative the desired nitrile is produced by rearrangement, with formation of the cyclobutene ring.

The starting substances of the formula IIb can be manufactured, for example, by condensing a compound of the formula

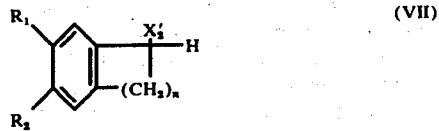

with a reactive functional derivative of a hydroxy compound of the formula HO—A—$X'_1$ (IIIa). Examples of reactive functional derivatives of compounds of the formula IIIa are derivatives of carbonic acid, such as carbon dioxide, phosgene, esters, for example di-lower alkyl esters of carbonic acid, halogenoformic acid derivatives, for example chloroformic acid lower alkyl esters or amides of chloroformic acid, such as its dimethylamide, and also cyanogen halides, such as cyanogen bromide.

Further reactive functional derivatives are α-halogeno-, such as α-bromo-lower alkanoic acids, for example bromoacetic acid, their esters, such as lower alkyl esters, amides, such as di-lower alkylamides, and nitriles. The condensation is carried out under the reaction conditions described earlier.

The starting substances of the formula IIc and salts thereof can be obtained, for example, by condensing a compound of the formula IIa with a reactive functional derivative of a hydroxy compound of the formula HO-A-$X''_1$ (IIIb) and converting a resulting compound of the formula IIc into another such compound within the defined scope.

Reactive functional derivatives of compounds of the formula IIIb, wherein A denotes the direct bond, are derivatives of hydrated formaldehyde, for example formaldehyde, paraformaldehyde or trioxane, and derivatives of carboxylic acids, for example of lower alkanoic acids, such as formic acid and acetic acid, or of benzoic acid, for example anhydrides, such as mixed anhydrides, for example with a hydrogen halide acid, such as hydrochloric acid. Examples thereof are acetyl chloride or benzoyl chloride. Further usable derivatives of the carboxylic acids are their esters, for example lower alkyl esters, such as ethyl esters. Hydroxy compounds of the formula IIIb, wherein A is a methylene group which is optionally substituted by a lower alkyl group, are ethylene glycols which are mono-lower alkylated at the carbon atom, or hydroxymethyl ketones, such as hydroxymethyllower alkyl ketones. Reactive functional derivatives thereof are above all reactive esters, for example with a hydrogen halide acid, such as with hydrobromic acid, for example ethylene bromohydrin or bromoacetone. The condensation is carried out, for example, under the reaction conditions described above. The conversions within the defined scope, for example, within the optionally esterified or amidised carboxyl group or within the substituents $R_1$ and $R_2$, can be carried out analogously to the corresponding conversions of the end products. For example, a hydroxymethyl group can be oxidised in a manner which is in itself known, for example by means of the calculated amount of chromic acid or by means of manganese dioxide, and be converted into the corresponding formyl group. A formyl group $X''_1$ can be converted into the hydroxymethyl group by reduction, for example with a complex hydride of boron or of aluminium, such as with sodium borohydride.

The starting substances of the formula IIc and salts thereof are, in turn, new compounds and a subject of the present application. They possess valuable pharmacological, especially anti-inflammatory and analgesic, activity, which can be demonstrated according to the methods described initially. Because of this activity the compounds of the formula IIc can be used as agents having an analgesic action, especially an anti-inflammatory action, above all for the treatment of arthritic symptoms.

For example, the compounds of the formula IIc are effective in the kaolin oedema test at about 10 to 100 mg/kg and in the writhing test at about 30 to about 300 mg/kg.

Preferred compounds of the formula IIc are those in which one of the groups $R_1$ and $R_2$ is hydrogen or halogen, especially chlorine, the other is cyclopentyl, cyclohexyl or cycloheptyl, $X_2$ denotes a free carboxyl group or carboxyl group esterified by lower alkyl, $X''_1$ denotes hydroxymethyl, A denotes a direct bond and n denotes 2, as well as pharmaceutically tolerated salts thereof.

1-Hydroxymethyl-5-cyclohexyl-6-chloro-1-indanecarboxylic acid is particularly preferred.

The starting substances of the formula IId can also be obtained from compounds of the formula IIa. For example, these are condensed with a functional derivative of an α-halogeno-malonic acid, such as α-chloromalonic acid or bromo-malonic acid, preferably with a diester, such as a di-lower alkyl ester, for example diethyl ester, for example with bromomalonic acid diethyl ester, or with a functional derivative of an α-acyl-α-halogenoacetic acid, for example an ester, such as lower alkyl ester, of an α-bromo-lower alkanoylacetic acid, for example α-bromo-acetoacetic acid ethyl ester. The condensation is preferably carried out under the same reaction conditions as the condensation with the compounds of the formula III. If desired, resulting derivatives of compounds of the formula IId, wherein A' denotes an unsubstituted methine group, can be converted into corresponding compounds wherein A' is methine substituted by a lower alkyl group. This conversion is preferably carried out by means of a reactive ester of a lower alkanol, for example with a hydrogen halide acid, such as hydrobromic acid or hydriodic acid, for example with methyl iodide, in the presence of a base, such as an alkali metal amide, hydride or lower alkanolate, for example lithium amide, sodium hydride or sodium ethylate.

Preferably, the reaction is carried out in a solvent, for example in an ether-like solvent, such as diethyl ether, or a lower alkanol, such as ethanol. The resulting compounds of the formula IId, wherein Y is an esterified carboxyl group, can be converted into the starting substances of the formula IId, wherein Y denotes the free carboxyl group, in the usual manner, for example by treatment with an alkali, such as sodium hydroxide, in water or a lower alkanol, such as ethanol, or with an aqueous acid, such as hydrochloric acid, through partial or complete saponification of the functionally modified malonic acid grouping, for example of the malonic ester grouping.

The new compounds of the present invention can be administered perorally, rectally or parenterally. Suitable unit dosage forms, such as dragees, tablets, suppositories or ampoules, preferably contain, as the active compound, 10–500 mg of a compound of the formula I or of a salt of a free acid, falling under this formula, with a pharmaceutically tolerated inorganic or organic base. In the unit dosage forms for peroral use, the content of active substance is preferably between 10 and 90%. To manufacture such unit dosage forms, the active compound is combined with, for example, solid, pulverulent excipients, such as lactose, sucrose, sorbitol, mannitol, starches, such as potato starch, corn starch or amylopectin, or laminaria powders or citrus pulp powders, cellulose derivatives or gelatine, optionally with addition of lubricants, such as magnesium stearate or calcium stearate or polyethylene glycols, to give tablets or dragee cores. The latter are coated, for example with concentrated sugar solutions which additionally contain, for example, gum arabic, talc or titanium dioxide, or with a lacquer dissolved in easily volatile organic solvents or solvent mixtures. Dyestuffs can be added to these coatings, for example to characterise different doses of active substance. Further suitable oral unit dosage forms are push-fit capsules of gelatine and soft, sealed capsules of gelatine and a plasticiser, such as glycerine. The former preferably contain the active compound as granules mixed with lubricants, such as talc or magnesium stearate, and optionally with stabilisers, such as sodium metabisulphite ($Na_2S_2O_5$) or ascorbic acid. In soft capsules, the active compound is preferably dissolved or suspended in suitable liquids, such as liquid polyethylene glycols, and again stabilisers can be added.

Examples of possible unit dosage forms for rectal use are suppositories which consist of a combination of an active compound with a suppositories base composition, based on natural or synthetic triglycerides (for example cacao butter), polyethylene glycols or suitable higher fatty alcohols, and gelatine rectal capsules which contain a combination of the active compound with polyethylene glycols.

Ampoule solutions for parenteral administration, especially intramuscular or intravenous administration, contain, for example, a compound of the general formula I at a concentration of, preferably, 0.5 – 5%, in the form of an aqueous dispersion prepared with the aid of customary solubilising agents and/or emulsifiers and optionally stabilisers, or an aqueous solution of a pharmaceutically tolerated watersoluble salt of a free acid falling under the general formula I.

Examples of further forms for parenteral administration are lotions, tinctures and ointments, prepared with the customary auxiliaries, for percutaneous use.

The instruction which follows is intended to explain in more detail the manufacture of tablets:

1,000 g of active compound, for example 1-methoxycarbonyl-5-cyclohexyl-6-chloro-1-indanecarboxylic acid, are mixed with 550 g of lactose and 292 g of potato starch and the mixture is moistened with an alcoholic solution of 8 g of gelatine and granulated through a sieve. After drying, 60 g of potato starch, 60 g of talc and 10 g of magnesium stearate and 20 g of highly disperse silica are mixed in and the mixture is pressed to give 10,000 tablets each weighing 200 mg and each containing 100 mg of active substance; the tablets can, if desired, be provided with breaking grooves for more accurate choice of the dosage.

The examples which follow explain the manufacture of the new compounds in more detail but are not intended in any way to restrict the scope of the invention.

EXAMPLE 1

30 ml of a 2.6 N solution of butyl-lithium in hexane are slowly added dropwise to a solution of 10.5 g of absolute diisopropylamine in 150 ml of absolute tetrahydrofurane at −15° C under a dry nitrogen atmosphere, whilst stirring. The mixture is left for a further 15 minutes at −15° C and 19.5 g of 5-cyclohexyl-6-chloro-1-indanecarboxylic acid methyl ester dissolved in 100 ml of absolute tetrahydrofurane are then added dropwise to this solution over the course of 15 minutes at −10° to −12° C. The mixture is stirred for a further 30 minutes at −15° to −5° C and thereafter a vigorous stream of dry carbon dioxide is passed through the reaction solution over the course of 10 minutes. The mixture is then evaporated to dryness in vacuo at room temperature and the residue is partitioned between cold saturated sodium bicarbonate solution and ether. The aqueous phase is then acidified with concentrated hydrochloric acid and extracted with ether. This ether phase is washed until neutral, dried over sodium sulphate and evaporated in vacuo. 1-Methoxycarbonyl-5-cyclohexyl-6-chloro-1-indanecarboxylic acid of melting point 139°–142° C crystallises from the evaporation residue on treatment with benzene-hexane.

The following compounds can be manufactured analogously:

1-Butoxycarbonyl-5-cyclohexyl-6-chloro-1-indanecarboxylic acid from 17 g of 5-cyclohexyl-6-chloro-1-indanecarboxylic acid butyl ester, 22 ml of a 2.6-N solution of butyl-lithium and carbon dioxide;

1-methoxycarbonyl-5-cycloheptyl-6-chloro-1-indanecarboxylic acid, melting point 144°–146° C (from benzene-hexane), from 15.5 g of 5-cycloheptyl-6-chloro-1-indanecarboxylic acid methyl ester, 22.4 ml of a 2.6 N solution of butyl-lithium and carbon dioxide;

1-propoxycarbonyl-5-cycloheptyl-6-chloro-1-indanecarboxylic acid, from 17 g of 5-cycloheptyl-6-chloro-1-indanecarboxylic acid propyl ester, 22 ml of a 2.6 N solution of butyl-lithium and carbon dioxide;

1-butoxycarbonyl-5-cycloheptyl-6-chloro-1-indanecarboxylic acid, melting point 118° C (from pentane), from 5.8 g of 5-cycloheptyl-6-chloro-1-indanecarboxylic acid butyl ester, 8 ml of a 2.6 N solution of butyl-lithium and carbon dioxide;

1-methoxycarbonyl-5-chloro-6-cyclohexyl-1-indanecarboxylic acid, from 16 g of 5-chloro-6-cyclohexyl-1-indanecarboxylic acid methyl ester, 22 ml of a 2.6 N solution of butyl-lithium and carbon dioxide;

1-methoxycarbonyl-5-cyclohexyl-1-indanecarboxylic acid, melting point (140°) 148°–152° C with decomposition (from etherhexane), from 13 g of 5 -cyclohexyl-1-indanecarboxylic acid methyl ester, 22.5 ml of a 2.6 N solution of butyl-lithium and carbon dioxide;

1-methoxycarbonyl-5-cycloheptyl-1-indanecarboxylic acid; melting point 140°–141° C (from pentane), from 10 g of 5-cycloheptyl-1-indanecarboxylic acid methyl ester, 12.8 ml of a 2.6 N solution of butyl-lithium and carbon dioxide.

EXAMPLE 2

15.4 ml of a 2.6 N solution of butyl-lithium (in hexane) are slowly added dropwise to a solution of 5.6 ml of absolute diisopropylamine in 40 ml of absolute tetrahydrofurane at −5° C under a nitrogen atmosphere, whilst stirring, and thereafter a solution of 8.0 g of 5-cyclohexyl-benzocyclobutene-1-carboxylic acid methyl ester in 40 ml of absolute tetrahydrofurane is added similarly. After completion of the addition the mixture is stirred for a further 15 minutes at −15° C and thereafter a vigorous stream of nitrogen (dried over concentrated sulphuric acid) is passed through the solution for 10 minutes, during which the colour of the solution changes from dark yellow to pale yellow. The reaction solution is partitioned between five times 40 ml of saturated sodium bicarbonate solution and 200 ml of ether. The combined aqueous phases are adjusted to pH 4 with concentrated hydrochloric acid at 0° C and extracted three times with 100 ml of methylene chloride at a time. The organic extracts are washed with water, dried over sodium sulphate and evaporated to dryness in vacuo. Using ether-pentane, 1-methoxycarbonyl-5-cyclohexyl-1-benzocyclobutene-carboxylic acid crystallises from the evaporated residue; melting point 140°–155° C.

EXAMPLE 3

23.6 ml of butyl-lithium (20% strength in hexane) are slowly added dropwise to a solution of 7.6 g of diisopropylamine (absolute) in 80 ml of absolute tetrahydrofurane at −10° to −15° C under a dry nitrogen atmosphere, whilst stirring, and 15 minutes after completion of the addition a solution of 15.5 g of 5-cyclohexyl-1-indanecarboxylic acid methyl ester in 40 ml of absolute tetrahydrofurane is added. The reaction solution is cooled to −20° C and a solution of 16.5 g of ethyl bromoacetate in 40 ml of absolute tetrahydrofurane is rapidly added dropwise. In the course thereof, the temperature rises to 0° C. The reaction solution is partitioned between three times 200 ml of methylene chloride and three times 200 ml of 2 N hydrochloric acid. The combined organic phase are washed with water, dried over sodium sulphate and evaporated in vacuo. Distillation of the evaporation residue in a high vacuum yields 1-methoxycarbonyl-5-cyclohexyl-1-indaneacetic acid ethyl ester in the fraction boiling at 140°–142° C/0.04 mm Hg.

EXAMPLE 4

A solution of 9.0 g of 1-methoxycarbonyl-5-cyclohexyl-1-indaneacetic acid ethyl ester in 100 ml of tetrahydrofurane and 500 ml of dioxane is treated with a solution of 29 ml of 1.0 N sodium hydroxide solution in 100 ml of methanol and the mixture is stirred for 24 hours at room temperature. The reaction mixture is evaporated in vacuo at 30° C to a volume of approx. 100 ml and is partitioned between twice 200 ml of water and twice 200 ml of ether. The combined aqueous phases are adjusted to pH 2 with concentrated hydrochloric acid and extracted with twice 200 ml of ether. The combined organic phases are washed with water, dried over sodium sulphate and evaporated to dryness in vacuo. The evaporation residue is chromatographed on a 20-fold amount of silica gel, with ether as the eluting agent. Fractions 5–15 (each of 50 ml) contain 1-methoxy-carbonyl-5-cyclohexyl-1-indaneacetic acid; melting point (127°) 135°–137° C (from etherpentane).

EXAMPLE 5

A solution of 3.0 g of 1-carbomethoxy-5-cyclohexyl-1-indaneacetic acid in 50 ml of dioxane and 20 ml of 2 N sodium hydroxide solution is boiled for 15 hours under reflux. It is evaporated in vacuo to a volume of 50 ml, adjusted to pH 2 with concentrated hydrochloric acid at 0° C and partitioned between twice 150 ml of 2 N hydrochloric acid and twice 100 ml of methylene chloride. The combined organic phases are washed with water, dried over sodium sulphate and evaporated to dryness in vacuo. The residue, in hot ethanol, is treated with active charcoal. The resulting 1-carboxy-5-cyclohexyl-1-indaneacetic acid crystallises from ethanol-water; melting point >206° C, with decomposition.

EXAMPLE 6

A vigorous stream of ammonia gas dried over potassium hydroxide is passed into a solution of 3.5 g of 1-methoxycarbonyl-5-cycloheptyl-1-indanecarboxylic acid chloride in 50 ml of absolute benzene for 5 minutes at 10° C, whilst stirring. The reaction mixture is then partitioned twice between 50 ml of ethyl acetate and 100 ml of ice-cold saturated sodium bicarbonate solution. The organic phases are washed with water, dried over sodium sulphate and evaporated in vacuo. The evaporation residue, when crystallised from ether/petroleum ether, yields 1-methoxycarbonyl-5-cycloheptyl-1-indanecarboxylic acid amide; melting point 136°–137° C.

The starting material can be obtained as follows:

A solution of 3.5 g of 1-methoxycarbonyl-5-cycloheptyl-1-indanecarboxylic acid in 50 ml of absolute benzene and 5 ml of thionyl chloride is boiled under reflux, with exclusion of water, for 1½ hours. After evaporation in vacuo, crude 1-methoxycarbonyl-5-cycloheptyl-1-indanecarboxylic acid chloride remains, which is processed further without additional purification.

EXAMPLE 7 a. 3.0 ml of dimethyl sulphide are added to a suspension of 4.0 g of N-chlorosuccinimide in 100 ml of absolute toluene under a nitrogen atmosphere, whilst stirring, and this is followed, at −25° C, by a solution of 6.45 g of 1-hydroxymethyl-5-cyclohexyl-6-chloro-1-indanecarboxylic acid methyl ester in 20 ml of absolute toluene. The mixture is stirred for a further 90 minutes at −25° C. 3.1 g of triethylamine are then added and the reaction solution is partitioned between 150 ml of ether and 100 ml of cold 1 N hydrochloric acid. The organic phases is washed until neutral, dried over sodium sulphate and evaporated in vacuo at room temperature. The crude oily 1-formyl-5-cyclohexyl-6-chloro-1-indanecarboxylic acid methyl ester contained in the evaporation residue is immediately processed further.

b. A solution of 3.0 g of crude 1-formyl-5-cyclohexyl-6-chloro-1-indanecarboxylic acid methyl ester in 30 of tetrahydrofurane and 3 ml of water is treated with 4 equivalents of silver oxide (manufactured according to Corey et al., J. Amer. Chem. Soc., 90, 5616 (1963)) and the mixture is stirred overnight at room temperature. The reaction solution is then filtered through Celite and the filtrate is partitioned between 150 ml of methylene chloride and 100 ml of 0.1 N hydrochloric acid. The organic phase is washed with twice 150 ml of water, dried over sodium sulphate and evaporated in vacuo. Chromatography of the evaporation residue on silica gel, using benzene/ethyl acetate/glacial acetic acid, 90:30:1, as the eluting agent, yields crude 1-methoxycarbonyl-5-cyclohexyl-6-chloro-1-indanecarboxylic acid which can be purified further by fractional crystallisation from benzene-hexane; melting point 139°–142° C.

Starting materials which can be used according to the invention can be manufactured as follows:

EXAMPLE 8

5 ml of concentrated sulphuric acid are added to a solution of 21 g of 5-cyclohexyl-6-chloro-1-indanecarboxylic acid in 300 ml of absolute methanol and the mixture is subsequently boiled for 4 hours under reflux, with exclusion of water. It is then evaporated in vacuo to a volume of 50 ml and partitioned between ether (twice 200 ml) and ice water (twice 200 ml). The organic phases are successively washed with aqueous sodium bicarbonate solution and water, dried over sodium sulphate and evaporated in vacuo. The evaporation residue is distilled in a high vacuum. The fraction which boils at 157° C/0.2 mm Hg contains 5-cyclohexyl-6-chloro-1-indanecarboxylic acid methyl ester.

The following can be manufactured analogously:

5-Cyclohexyl-6-chloro-1-indanecarboxylic acid butyl ester from 21 g of 5-cyclohexyl-6-chloro-1-indanecarboxylic acid, 300 ml of absolute butanol and 5 ml of concentrated sulphuric acid;

5-chloro-6-cyclohexyl-1-indanecarboxylic acid methyl ester from 21 g of 5-chloro-6-cyclohexyl-1-indanecarboxylic acid, 300 ml of absolute methanol and 300 ml of concentrated sulphuric acid;

5-cyclohexyl-1-indanecarboxylic acid methyl ester from 40 g of 5-cyclohexyl-1-indanecarboxylic acid, 400 ml of absolute methanol and 8 ml of concentrated sulphuric acid.

EXAMPLE 9 a. 10 g of 10% strength palladium on charcoal are added to a solution of 102 g of p-(cyclohepten-1-yl)-acetophenone in 1 l of ethanol and the mixture is hydrogenated at room temperature and normal pressure until 1 equivalent of hydrogen has been taken up. The catalyst is then fltered off and the filtrate is evaporated to dryness in vacuo. The p-cycloheptyl-acetophenone contained in the evaporation residue is further processed in the crude form.

b. 177 g of crude p-cycloheptyl-acetophenone are dissolved in 320 ml of concentrated sulphuric acid at 0° C whilst stirring and a solution of 90 ml of 65% strength nitric acid in 213 ml of concentrated sulphuric acid is then added dropwise at 0° C (period of addition: 3 hours). Thereafter the mixture is stirred for a further hour at 0° to 5° C. The reaction mixture is then poured onto 5 kg of ice and extracted 3 times with 1 l of ethyl acetate at a time. The organic phases are successively washed with 2% strength sodium hydroxide solution and water whilst cooling with ice, and are dried over sodium sulphate and evaporated in vacuo. The crude 3-nitro-4-cycloheptyl-acetophenone which remains in the evaporation residue is immediately processed further in the crude form.

c. 16 g of Rupe nickel are added to a solution of 160 g of crude 3-nitro-4-cycloheptyl-acetophenone in 2 l of ethanol and the compound is hydrogenated under normal pressure at 25° C until 3 equivalents of hydrogen have been taken up. The catalyst is then filtered off and the filtrate is evaporated to dryness in vacuo. The viscous black oil which remains in the residue is extracted 3 times with 500 ml of ether/petroleum ether (1:1) at a time. The extracts are treated with active charcoal and evaporated to dryness in vacuo. The yellow-red oil which remains in the evaporation residue contains 3-amino-4-cycloheptyl-acetophenone and is directly processed further, without additional purification.

d. A solution of 5 g of sodium nitrite in 20 ml of water is slowly added dropwise at 0° C, whilst stirring, to a solution of 11 g of crude 3-amino-4-cycloheptyl-acetophenone in 70 ml of concentrated hydrochloric acid. After completion of the addition the mixture is stirred for a further 30 minutes at 0° C. The reaction solution is then added dropwise at 0° to 5° C, whilst stirring, to a solution of 7 g of freshly prepared copper-(I) chloride in 30 ml of concentrated hydrochloric acid. After completion of the addition, the mixture is stirred for a further hour at room temperature and a further hour at 40° to 50° C. The reaction mixture is now extracted three times with 200 ml of ether at a time. The organic phases are successively washed with water, 2 N sodium hydroxide solution and again with water, dried over sodium sulphate and evaporated in vacuo. Distillation of the evaporation residue in a high vacuum yields crude 3-chloro-4-cycloheptyl-acetophenone in the fraction boiling at about 130° C/0.05 mm Hg.

e. 14.5 ml of bromine are slowly added dropwise to a solution of 38 g of sodium hydroxide in 160 ml of water at 0° C, whilst stirring, a solution of 12.5 g of 3-chloro- 4-cycloheptylacetophenone in 150 ml of dioxane is then added at 30°–40° C and the mixture is left to stand overnight at room temperature. 30 g of sodium bisulphite are then added in portions to the reaction solution, whilst cooling, and the reaction solution is evaporated in vacuo to a volume of about 150 ml. The reaction solution is now diluted with water to a volume of 500 ml and acidified with concentrated hydrochloric acid whilst cooling well, and the crude 3-chloro-4-cycloheptyl-benzoic acid is filtered off. This crude material is dissolved in a large amount of chloroform. The organic phase is then washed with water, dried over sodium sulphate and evaporated to dryness in vacuo. Using petroleum ether, 3-chloro-4-cycloheptylbenzoic acid, of melting point 117°–120° C, crystallises from the evaporation residue.

f. A solution of 11.7 g of 3-chloro-4-cycloheptylbenzoic acid in 100 ml of chloroform and 10 ml of thionyl chloride is boiled for 4 hours under reflux, with exclusion of water. It is then evaporated to dryness in vacuo. The crude oily 3-chloro-4-cycloheptyl-benzoyl chloride contained in the evaporation residue is dissolved in 100 ml of benzene. Dry ammonia gas is passed into this solution for 1½ hours whilst stirring. The precipitate formed is now filtered off and recrystallised from ethanol-methanol-water. 3-Chloro-4-cycloheptyl-benzamide is thus obtained; melting point 152°–155° C.

g. A solution of 7.3 g of 3-chloro-4-cycloheptylbenzamide in 50 ml of phosphorus oxychloride is boiled for 12 hours under reflux, with exclusion of water. The excess phosphorus oxychloride is then distilled off in vacuo. 200 ml of ice water are added to the evaporation residue, which is rendered alkaline with saturated sodium carbonate solution and extracted three times with 100 ml of methylene chloride at a time. The organic phases are washed until neutral, dried over sodium sulphate, treated with active charcoal, filtered and evaporated in vacuo. The crude 3-chloro-4-cycloheptylbenzonitrile contained in the evaporation residue is directly processed further, without additional purification.

h. Anhydrous hydrochloric acid gas is passed into a suspension of 8.5 g of tin-(II) chloride (anhydrous) in 60 ml of absolute ether, whilst stirring and excluding water, until 2 clear phases form. 6.7 g of 3 chloro-4-cycloheptyl-benzoic acid nitrile are added to this mixture, dry hydrochloric acid gas is passed in over the course of a further 2 hours, whilst stirring, and thereafter the mixture is left to stand overnight at room temperature. It is then evaporated to dryness in vacuo, 150 ml of water are added to the evaporation residue, and the whole is boiled for 1 hour under reflux. It is now allowed to cool to room temperature and extracted three times with 100 ml of chloroform at a time. The organic phases are washed until neutral, dried over sodium sulphate and evaporated in vacuo. The evaporation residue is distilled in a high vacuum. The fraction boiling at 120°–122° C/0.07 mm Hg contains the 3-chloro-4-cycloheptyl-benzaldehyde.

i. A solution of 26.7 g of 3-chloro-4-cycloheptylbenzaldehyde, 1 g of benzoic acid, 1 ml of piperidine and 26 g of malonic acid diethyl ester in 200 ml of benzene is boiled for 5 hours under reflux, in a water separator. The reaction solution is then allowed to cool to room temperature and washed successively with 150 ml of 1 N hydrochloric acid and 150 ml of saturated sodium bicarbonate solution. The organic phase is washed until neutral, dried over sodium sulphate and evaporated in vacuo. Distillation of the evaporation residue in a high vacuum yields α,α-[3-chloro-4-cycloheptyl-benzylidene]-malonic acid diethyl ester in the fraction boiling at 180°–185° C/0.04 mm.

j. A solution of 6.25 g of potassium cyanide in 10 ml of water is added to a solution of 34.1 g of α,α-[3-chloro-4-cycloheptyl-benzylidene]-malonic acid diethyl ester in 300 ml of absolute ethanol at 55° C and the mixture is stirred for 2 hours at 55° C. It is then cooled to room temperature, the precipitate produced is filtered off and the filtrate is neutralised with 2 N hydrochloric acid and evaporated to dryness in vacuo. The evaporation residue is partitioned between 400 ml of ether and ice-cold saturated sodium bicarbonate solution and the sodium bicarbonate solution is separated off and extracted twice with 400 ml of ether at a time. The organic phases are washed until neutral, dried over sodium sulphate and evaporated to dryness in vacuo. The crude 3-(3-chloro-4-cycloheptylphenyl)-3-cyano-propionic acid ethyl ester which has remained in the evaporation residue is directly processed further, without additional purification.

k. A solution of 19 g of the crude 3-(3-chloro-4-cycloheptyl-phenyl)3-cyano-propionic acid ethyl ester in 150 ml of concentrated hydrochloric acid and 250 ml of glacial acetic acid is boiled for 15 hours under reflux. It is then evaporated in vacuo to a volume of about 100 ml and 400 ml of water are added to the residue, and the mixture is extracted three times with 400 ml of ether at a time. The organic phases are washed until neutral, dried over sodium sulphate and evaporated in vacuo. Using petroleum ether, 2-(3-chloro-4-cycloheptylphenyl)-succinic acid crystallises from the evaporation residue; melting point 150°–152° C.

l. A solution of 14.0 g of 2-[3-chloro-4-cycloheptylphenyl]-succinic acid and 12 ml of thionyl chloride in 120 ml of absolute toluene is boiled for 2 hours under reflux, with exclusion of water. It is then evaporated to dryness in vacuo. The evaporation residue, crude 2-[3-chloro-4-cycloheptyl-phenyl]-succinic anhydride, is added in portions to a stirred suspension of 26 g of powdered aluminium chloride in 200 ml of absolute carbon disulphide at 15°–20° C, with exclusion of water. After completion of the addition, the mixture is stirred for a further hour at 20° C and a further hour at 35° C. The reaction mixture is then allowed to cool to room temperature over the course of 1½ hours and is added to 50 ml of concentrated hydrochloric acid in 500 g of ice, and the mixture is extracted three times with 200 ml of ether at a time. The organic phases are washed until neutral, dried over sodium sulphate, treated with active charcoal, filtered and evaporated to dryness in vacuo. Using ether/carbon tetrachloride, 3-oxo-5-cycloheptyl-6-chloro-1-indanecarboxylic acid, melting point 157°–160° C, crystallises from the evaporation residue.

m. 1.52 g of sodium borohydride are added in portions to a solution of 12.0 g of 3-oxo-5-cycloheptyl-6-chloro-1-indanecarboxylic acid in a mixture of 30 ml of dioxane, 150 ml of saturated sodium bicarbonate solution and 300 ml of water at 10° C, whilst stirring, and the mixture is left to stand for 6 hours at room temperature. The reaction solution is then acidified by dropwise addition of concentrated hydrochloric acid and is extracted twice with 180 ml of methylene chloride at a time and twice with 200 ml of ethyl acetate at a time. The organic phases are washed until neutral, dried over sodium sulphate and evaporated in vacuo. 3-Hydroxy-5-cycloheptyl-6-chloro-1-indanecarboxylic acid remains in the evaporation residue; melting point 169°–171° C.

n. A solution of 12 g of 3-hydroxy-5-cycloheptyl-6-chloro-1-indanecarboxylic acid in 150 ml of glacial acetic acid and 50 ml of concentrated hydrochloric acid is boiled under reflux for 30 minutes. Water is added to the solution, whilst it is still hot, until it turns turbid, and the mixture is allowed to cool to room temperature. The crude 5-cycloheptyl-6-chloro-1-indene-1-carboxylic acid which has precipitated is then filtered off; after one recrystallisation from ethanol/petroleum ether it melts at 205°–208° C.

o. A solution of 1 g of 5-cycloheptyl-6-chloro-ind-1-ene-1-carboxylic acid in 40 ml of absolute ethanol is hydrogenated with 100 mg of Raney nickel at room temperature and normal pressure until 1 equivalent of hydrogen has been taken up. The catalyst is then filtered off, the filtrate is evaporated to dryness in vacuo and the residue is crystallised from ether/petroleum ether. 5-Cycloheptyl-6-chloro-1-indanecarboxylic acid, thus obtained, melts at 138°–140° C.

p. 5-Cycloheptyl-6-chloro-1-indanecarboxylic acid methyl ester is manufactured analogously to Example 8 from 16.3 g of 5-cycloheptyl-6-chloro-1-indanecarboxylic acid, 250 ml of absolute methanol and 5 ml of concentrated sulphuric acid, and can be further processed in the crude state; boiling point 170° C/0.1 mm Hg.

Analogously to p), 5-cycloheptyl-6-chloro-1-indanecarboxylic acid propyl ester can be manufactured from 16.3 g of 5-cycloheptyl-6-chloro-1-indanecarboxylic acid, 250 ml of absolute propanol and 5 ml of concentrated sulphuric acid.

Analogously to p), 5-cycloheptyl-6-chloro-1-indanecarboxylic acid butyl ester can be manufactured from 16 g of 5-cycloheptyl-6-chloro-1-indanecarboxylic acid, 150 ml of absolute butanol and 1 ml of concentrated sulphuric acid; boiling point approx. 170°–180° C/0.1 mm Hg.

Cycloheptylbenzaldehyde can be manufactured as follows: 200 ml of titanium tetrachloride are added dropwise, whilst stirring, to a solution of 200 g of cycloheptylbenzene in 600 ml of absolute methylene chloride under a nitrogen atmosphere at −10° C, and thereafter 132.5 g of dichloromethyl ether are added similarly at 0° C. The reaction mixture is then stirred for a further 30 minutes at 10° C and poured onto 3 kg of ice, and the whole is extracted twice with 500 ml of methylene chloride. The organic phases are washed with water, dried over sodium sulphate and evaporated to dryness in vacuo. Distillation of the evaporation residue in a high vacuum yields 4-cycloheptyl-benzaldehyde in the fraction boiling at 120°–130° C/0.8 mm Hg.

Analogously to i), α,α-(4-cycloheptyl-benzylidene)-malonic acid ester can be obtained starting from 284.5 g of 4-cycloheptyl-benzaldehyde, 43 g of benzoic acid, 28.5 ml of piperidine and 284.5 g of malonic acid diethyl ester; boiling point approx. 200° C/0.5 mm Hg.

Analogously to j), 3-(4-cycloheptyl-phenyl)-3-cyano-propionic acid ethyl ester can be obtained starting from 120 g of α,α-(4-cycloheptyl-benzylidene)-malonic acid diethyl ester and 24 g of potassium cyanide; it can be further processed in the crude state.

Analogously to k), 2-(4-cycloheptyl-phenyl)-succinic acid can be obtained starting from 200 g of 3-(4-cycloheptyl-phenyl)-3-cyano-propionic acid ethyl ester, 750 ml of concentrated hydrochloric acid and 750 ml of glacial acetic acid; melting point 156°–157° C.

Analogously to 1), 2-(4-cycloheptyl-phenyl)-succinic anhydride can be obtained starting from 139.3 g of 2-(4-cycloheptyl-phenyl)-succinic acid and 100 ml of thionyl chloride; melting point 141° C (from methylene chloride/hexane). 57 g of this anhydride can be converted by means of 70 g of powdered aluminum chloride in 350 ml of absolute nitrobenzene into 3-oxo-5-cycloheptyl-1-indanecarboxylic acid; melting point 102°–104° C.

5-Cycloheptyl-1-indanecarboxylic acid can be manufactured as follows:

A solution of 38 g of 3-oxo-5-cycloheptyl-1-indanecarboxylic acid in 400 ml of glacial acetic acid is hydrogenated with 12 g of palladium on charcoal (5% strength) under normal pressure and at room temperature, until 2 equivalents of hydrogen have been taken up. The catalyst is then filtered off and the filtrate is evaporated to dryness in vacuo. 5-Cycloheptyl-indane-1-carboxylic acid of melting point 116°–117° C crystallises from hexane on cooling.

Analogously to p), 5-cycloheptyl-1-indanecarboxylic acid methyl ester can be obtained starting from 60 g of 5-cycloheptyl-1-indanecarboxylic acid, 1,000 ml of absolute methanol and 10 ml of concentrated sulphuric acid; boiling point 165° C/0.04 mm Hg.

Example 10 a. 102 g of 3-chloro-4-cyclohexyl-phenylacetic acid (T.Y. Shen, Chimie Therapeutique 1967, No. 6, page 459) are dissolved in 1.4 l of absolute methanol. The solution is saturated with HCl gas at 0°–5° C and is then left to stand overnight at room temperature. The excess methanol is distilled off in vacuo. The residue is dissolved in ether and the acid removed with aqueous sodium bicarbonate solution. The ether solution is dried over sodium sulphate, filtered and evaporated. The oily residue, 105 g of 3-chloro-4-cyclohexyl-phenylacetic acid methyl ester, can be further processed in the crude state.

b. 105 g of crude 3-chloro-4-cyclohexylphenylacetic acid methyl ester are dissolved in 2.4 l of absolute ether and the solution is added dropwise, whilst stirring, to a solution of 15 g of lithium aluminum hydride in 800 ml of absolute ether, at 5°–10° C internal temperature. The reaction mixture is stirred for 3 hours at room temperature and is then carefully decomposed with 15 ml of water, 15 ml of 15 per cent strength aqueous sodium hydroxide solution and finally 45 ml of water. The solids are removed from the reaction product by filtration. The filtrate is dried over sodium sulphate and evaporated in vacuo. The oily residue, 98 g of crude β-(3-chloro-4-cyclohexyl-phenyl)-ethanol, can be directly reacted with thionyl chloride.

c. 38.5 g of crude β-(3-chloro-4-cyclohexyl-phenyl)-ethanol are dissolved in 13.2 ml of absolute pyridine and 20.3 g of thionyl chloride are added dropwise at an internal temperature not exceeding 40° C. Thereafter the temperature is gradually raised to 100°–110° C and the mixture is stirred for 2 hours at this temperature. The reaction mixture is then cooled to 20° C and diluted with ether and chloroform. The solution is twice washed with cold 2 N sodium carbonate solution, three times with 2 N hydrochloric acid and finally once more with 2 N sodium carbonate solution, dried over sodium sulphate and evaporated. The residue, 41.6 g of β-(3-chloro-4-cyclohexyl-phenyl)-ethyl chloride, can be converted into the nitrile without purification. However, it can easily be distilled at 0.06 mm Hg and 115°–117° C.

d. 63 g of distilled β-(3-chloro-4-cyclohexyl-phenyl)-ethyl chloride are dissolved in 630 ml of dimethylsulphoxide and added dropwise, whilst stirring, to a solution of 38.5 g of sodium cyanide in 380 ml of dimethylsulphoxide at 40° C. Thereafter the mixture is stirred for approx. 1¼ hours at 80° C internal temperature and cooled, and approx. 2 l of ice water are added. The nitrile is extracted with ether/methylene chloride. The solution is washed with water, dried over sodium sulphate, filtered and evaporated. The residue, 58.5 g, is distilled in a high vacuum: boiling point 135°–150° C/0.1 mm Hg; 52.7 g of colourless oily 1-(2-cyanoethyl)-3-chloro-4-cyclohexyl-benzene.

e. 52.7 g of distilled 1-(2-cyano-ethyl)-3-chloro-4-cyclohexyl-benzene are added dropwise over the course of 2-3 minutes to a solution of potassium amide prepared from 37 g of potassium metal in 500 ml of liquid ammonia and a pinch of iron trinitrate. After 30 minutes, 60 g of solid ammonium chloride are introduced in portions. The ammonia is allowed to evaporate overnight whilst stirring. Approx. 250 ml of water are added to the residue, which is extracted three times with ether. The ether solution is washed five times with water, dried over sodium sulphate and evaporated. The residue, 46 g of dark brown oil, is chromatographed on 460 g of silica gel (0.05–0.2 mm, highest purity, Merck Ag). The fractions eluted with benzene are practically pure 1-cyano-5-cyclohexyl-benzocyclobutene. Yield, 38-40 g of brownyellow oil. It can be distilled in small portions in a molecular path distillation apparatus; boiling point 130°–140° C/0.05 mm Hg.

f. 6.5 g of distilled 1-cyano-5-cyclohexylenzocyclobutene in 13 ml of ethanol and 40 ml of 20 per cent strength aqueous sodium hydroxide solution are boiled for 7 hours under reflux. The excess ethanol is distilled off in vacuo. The residue is dissolved in approx. 50 ml of water and cold dilute hydrochloric acid is added. The carboxylic acid is extracted with ether/methylene chloride. The solution is extracted three times with 2 N sodium carbonate solution. The sodium carbonate solution is acidified with 2 N hydrochloric acid whilst cooling with ice and the 5-cyclohexyl-1-benzocyclobutenecarboxylic acid which has precipitated is extracted with methylene chloride. The solution is washed with water, dried over sodium sulphate, filtered and evaporated. The viscous, oily residue of 5-cyclohexyl-1-benzocyclobutenecarboxylic acid is dried in a high vacuum at 60°–65° C.

The nuclear resonance spectrum (CDCl$_3$, 60 Mc) of the acid shows the following bands:
1.0–2.0 PPM, multiplet 10 H (cyclohexyl radical)
2.2–2.8 PPM, multiplet 1 H (benzyl-H of the cyclohexyl radical)
3.3–3.5 PPM, doublet 2 H (methylene-H of the four-membered ring)
4.1–4.4 PPM, triplet 1 H (α-H next to the carboxyl group on the four-membered ring)
6.7–7.3 PPM, multiplet 3 H (aromatic H)
approx. 9 PPM, singlet 1 H (carboxy-H)

g. A solution of 15 g of 5-cyclohexyl-1-benzocyclobutenecarboxylic acid in 150 ml of absolute methanol and 1.5 ml of concentrated sulphuric acid is boiled for 14 hours under reflux whilst excluding water. The reaction mixture is evaporated in vacuo at 30° C to a volume of approx. 30 ml and the evaporation residue is partitioned between three times 200 ml of ether and twice 200 ml of ice water. The combined organic phases are successively washed with saturated sodium bicarbonate solution and water, dried over sodium sulphate and evaporated in vacuo. Distillation of the evaporation residue in a high vacuum yields 5-cyclohexyl-1-benzocyclobutenecarboxylic acid methyl ester in the fraction boiling at approx. 150° C/0.07 mm Hg.

Example 11 a. A mixture of 245.3 g of m-bromo-acetophenone, 205 g of ethylene glycol, 4.1 g of p-toluenesulphonic acid, 2.1 litres of benzene and 4 drops of concentrated sulphuric acid is boiled under reflux for approx. 35 hours. The water produced in the ketalisation is removed from the reaction mixture by means of a water separator. 3 ml of absolute pyridine are then added to the hot solution, and the latter is allowed to cool. 200 ml of saturated sodium carbonate solution are then added to the mixture whilst stirring, and the organic phase is separated off. The latter is again washed with 100 ml of saturated sodium carbonate solution and subsequently with water, dried over sodium sulphate, filtered and evaporated. The oily residue, m-bromoacetophenoneethylene-ketal, can be directly processed further.

b. 14.3 g of magnesium filings are washed twice with chloroform and dried hot in vacuo. A few crystals of iodine are then added and the mixture is heated in vacuo. The magnesium activated in this way is first introduced into a stirred flask, and is covered with 200 ml of absolute tetrahydrofurane. This mixture is warmed to approx. 65°–70° C, and approx. 30 ml of a solution prepared from 140 g of m-bromoacetophenone-ethylene-ketal and 140 ml of absolute tetrahydrofurane is allowed to run in. The mixture is left until the Grignard reaction starts (approx. 5–10 minutes) and the rest of the ketal solution is then added dropwise in such a way that the internal temperature does not exceed 70° C. Thereafter the reaction mixture is stirred for 1 hour at 65°–70° C, cooled to 20° C and diluted with 300 ml of absolute tetrahydrofurane. 49.0 g of cyclohexanone are then added dropwise whilst stirring and cooling with ice. In the course thereof, the temperature of the solution should not rise above 30° C. After the addition, the mixture is stirred for a further hour at 30°–40° C. The solvent is now removed in vacuo at 40° C and 450 ml of a saturated ammonium chloride solution and ice are added to the residue. The mixture is then extracted four times with 250 ml of ether at a time. The ether phase is washed once with aqueous ammonium chloride solution and once with sodium carbonate solution, dried over sodium sulphate, filtered and evaporated. The residue a yellow oil, is distilled at 0.05 mm Hg; at 128°–136° C, an oil passes over, which can be caused to crystallise from ether-petroleum ether. 2-[m-(1-Hydroxycyclohexyl)-phenyl]-2-methyl-1,3-dioxolane is thus obtained as white crystals of melting point 55°–57° C.

c. 26.5 g of this product are dissolved in 265 ml of glacial acetic acid and 13 ml of concentrated hydrochloric acid and 26.5 ml of water are added. This mixture is stirred for 1 hour at 60° C internal temperature and is then diluted with 500 ml of water at room temperature. The reaction mixture is then extracted with ether. The ether phase is repeatedly extracted by shaking with 70 ml portions of 1 N sodium hydroxide solution, washed with water until neutral, dried over sodium sulphate, filtered and evaporated. The residue, a light brown oil, on distillation yields m-(1-cyclohexenyl)-acetophenone as a colourless liquid of boiling point 116°–118° C/0.1 mm Hg.

d. 37.6 g of distilled m-(1-cyclohexenyl)-acetophenone in 450 ml of ethyl acetate are hydrogenated in the presence of 3.7 g of 5 per cent strength palladium on calcium carbonate in a hydrogen atmosphere under normal pressure. After 10 minutes, 4.2 litres of hydrogen have been taken up; the hydrogenation is then stopped. The catalyst is filtered off and the solution is evaporated. The residue, a colourless oil, is practically pure m-cyclohexyl-acetophenone and can be employed without further purification for the subsequent reaction.

e. A mixture of 49.4 g of m-cyclohexyl-acetophenone, 15.6 g of sulphur and 42.4 g of morpholine is boiled for 3 hours at a bath temperature of 130°–140° C. The reaction mixture is then poured into 200 ml of hot absolute alcohol. On scratching, a little sulphur of melting point 114°–7° C crystallises. This is filtered off and the filtrate is evaporated in vacuo. 100 ml of toluene at a time are distilled from the residue three times in vacuo. The residue, a dark brown oil, does not require further purification. It contains m-cyclohexyl-phenyl-thioacetmorpholide.

f. A mixture of 76.8 g of the crude morpholide, 155 g of a 50 per cent strength aqueous potassium hydroxide solution and 275 ml of ethanol is boiled for 6 hours under reflux. The ethanol is then distilled off in vacuo and the residue is dissolved in water. This solution is treated with animal charcoal and filtered through diatomaceous earth (Celite). The brown filtrate is acidified with concentrated hydrochloric acid whilst cooling with ice. The oil which separates out is taken up in ether. The ether phase is washed with water until neutral, dried over sodium sulphate, filtered and evaporated. The crystalline residue is taken up in ether and converted into the sodium salt by means of saturated aqueous sodium carbonate solution. The aqueous solution is acidified with concentrated hydrochloric acid whilst cooling with ice. The acid, which only partially precipitates as crystals, is taken up in ether. The ether solution is washed with water, dried over sodium sulphate, filtered and evaporated. The m-cyclohexyl-phenylacetic acid which remains slowly crystallises to give a solid of melting point 68°–74° C.

g. Hydrogen chloride is passed into a solution of 56.2 g of m-cyclohexyl-phenylacetic acid in 750 ml of absolute methanol at 0° C. This solution is left to stand overnight and is then evaporated in vacuo. The residue is taken up in ether. The ether phase is neutralised with aqueous sodium carbonate solution, dried over sodium sulphate, filtered and evaporated. The dark brown oil is distilled in a high vacuum. Hereupon, m-cyclohexyl-phenylacetic acid methyl ester passes over as a colourless oil of boiling point 117°–135° C/0.07 mm Hg.

h. 40.0 g of m-cyclohexyl-phenylacetic acid methyl ester in 860 ml of absolute ether are added dropwise to 5.75 g of lithium aluminium hydride in 290 ml of absolute ether, whilst cooling with ice and stirring. Thereafter the mixture is stirred for 4 hours at room temerature. 5.8 ml of water, 5.8 ml of 15 per cent strength sodium hydroxide solution and finally 17 ml of water are then carefully added to the reaction mixture. The whole is filtered through diatomaceous earth (Celite) and the filtrate is dried over sodium sulphate, filtered and evaporated. The residue, a light yellow oil, is distilled in a high vacuum, whereupon colourless β-(m-cyclohexyl-phenyl)-ethanol of boiling point 115°–8° C/0.03 mm Hg is obtained.

i. 33.1 g of β-(m-cyclohexyl-phenyl)-ethanol are mixed with 13.3 ml of absolute pyridine. 12.5 ml of thionyl chloride are added dropwise to this mixture, whilst cooling with ice. Thereafter the reaction mixture is slowly heated to 100°–110° C and is kept at this temperature for 2 hours. The reaction solution is again cooled to room temperature, 29 ml of water are added and the whole is extracted with a mixture of ether and chloroform. The organic phase is washed twice with 2 N sodium carbonate solution, three times with 2 N hydrochloric acid and finally once with 2 N sodium carbonate solution, dried over sodium sulphate, filtered and evaporated. The residue, a brown oil, is distilled in a high vacuum. Hereupon, β-m-cyclohexyl-phenyl)-ethyl chloride is obtained as a light yellow oil of boiling point 103°–8° C/0.1 mm Hg.

j. 3.56 ml of bromine (1 drop/5 seconds) are added dropwise to a mixture of 14.4 g of β-(m-cyclohexyl-phenyl)-ethyl chloride and 65 mg of iodine, whilst cooling with water. Thereafter the reaction mixture is left to stand for 65 hours at room temperature and is then taken up in ether, and the ether phase is extracted by shaking 3 times with water, 3 times with 2 N sodium carbonate solution and twice with 5 per cent strength sodium thiosulphate solution, dried over sodium sulphate, filtered and evaporated. The light yellow oil which remains consists of a 4:1 mixture of β-(2-bromo-5-cyclohexyl- and β-(4-bromo-3-cyclohexyl-phenyl)-ethyl chloride.

k. A solution of 21.9 g of a mixture of the isomeric β-(bromo-cyclohexyl-phenyl)-ethyl chlorides in 220 ml of dimethylsulphoxide is added dropwise to 13.4 g of powdered sodium cyanide in 135 ml of dimethylsulphoxide at 40° C, whilst stirring. Thereafter the mixture is stirred for a further 1½hours at 80° C. The reaction mixture is allowed to cool to room temperature and 700 ml of ice water are added. The reaction mixture is then extracted with a mixture of methylene chloride and ether. The organic phase is washed six times with water, dried over sodium sulphate, filtered and evaporated. The light brown residue is chromatographed on a ten-fold amount of silica gel. Using benzene as a running agent, 15.0 g of a mixture of the isomeric β-(2-bromo-5-cyclohexyl- and β-(4-bromo-3-cyclohexyl-phenyl)-propionitriles are eluted.

This mixture can be cyclised without a further purification operation.

l. 15 g of chromatographed isomer mixture of β-(2-bromo-5-cyclohexyl- and β-(4-bromo-3-cyclohexyl-phenyl)-propionitrile are added dropwise over the course of 2-3 minutes to a solution of sodium amide prepared from 5.3 g of sodium metal in 150 ml of liquid ammonia and 100 mg of iron trinitrate. After 15 minutes, 15 g of solid ammonium chloride are introduced portions. The ammonia is allowed to evaporate overnight whilst stirring. 100 ml of water are added to the residue and the mixture is extracted three times with ether. The ether solution is washed five times with water, dried over sodium sulphate and evaporated. The residue, a dark brown oil, is chromatographed on 114 g of silica gel (0.05–0.2 mm, highest purity, Merck AG). The fractions eluted with benzene are practically pure 1-cyano-4-cyclohexyl-benzocyclobutene.

m. 6.6 g chromatographed 1-cyano-4-cyclohexylbenzocyclobutene in 40 ml of ethanol and 40 ml of 20 per cent strength aqueous sodium hydroxide solution are boiled for 7 hours under reflux. The excess ethanol is distilled off in vacuo. The residue is dissolved in approx. 50 ml of water and cold dilute hydrochloric acid is added. The carboxylic acid is extracted with ether/methylene chloride. The solution is extracted 3 times with 2 N sodium carbonate solution. The sodium carbonate solution is acidified with 2 N hydrochloric acid whilst cooling with ice and the oily 4-cyclohexyl-benzocyclobutene-1-carboxylic acid which precipitates is extracted with methylene chloride. The solution is washed with water, dried over sodium sulphate, filtered and evaporated. The residue crystallises overnight. It is dissolved in 27 ml of 1 N sodium hydroxide solution. The residue which remains after the evaporation of this solution is dissolved in hot ethanol and caused to crystallise by means of acetone-ether. The sodium salt of 4-cyclohexyl-1-benzocyclobutenecarboxylic acid is thus obtained as light yellow crystals of melting point 270° C.

n. Analogously to Example 10 g), 4-cyclohexyl-1-benzocyclobutenecarboxylic acid methyl ester can be prepared from 15 g of 4-cyclohexyl-1-benzocyclobutenecarboxylic acid, 150 ml of absolute methanol and 1.5 ml of concentrated sulphuric acid.

EXAMPLE 12 a. A solution of 200 g of 3-chloro-4-cyclohexylbenzoic acid in 1 l of methanol and 20 ml of concentrated sulphuric acid is boiled for 2 hours under reflux, with exclusion of water. It is then evaporated in vacuo to a volume of about 500 ml. 1 l of ice water and 1 l of ether are added to the concentrated solution and the ice water layer is extracted 2 with 1 l of ether. The organic phases are washed 2 with 1 l of ice water at a time and 2 with 500 ml of saturated sodium bicarbonate solution at a time and then twice more with 500 ml of water at a time, dried over sodium sulphate and evaporated to dryness in vacuo. The evaporation residue contains the crude oily 3-chloro-4-cyclohexyl-benzoic acid methyl ester.

b. A solution of 200 g of crude 3-chloro-4-cyclohexylbenzoic acid methyl ester in 600 ml of absolute dioxane is added dropwise to a suspension of 33 g of lithium aluminium hydride in 1.2 l of absolute dioxane at 80° C, whilst stirring and excluding water, and after completion of the addition the mixture is stirred for a further 2 hours at the same temperature. It is then cooled to 0° C and the excess reducing agent is destroyed dropwise with water, whilst cooling with ice. The aluminium hydroxide formed is now filtered off. Evaporation of the filtrate in vacuo yields crude 3-chloro-4-cyclohexyl-benzyl alcohol in the residue.

c. 50 ml of thionyl chloride are added in portions to a solution of 108 g of 3-chloro-4-cyclohexyl-benzyl alcohol in 800 ml of absolute benzene, whilst stirring and excluding water, and the mixture is left to stand for 2 hours at room temperature. It is then evaporated to dryness in vacuo at below 30° C. Crude 3-chloro-4-cyclohexyl-benzyl chloride is left in the evaporation residue.

d. 27.6 g of sodium are dissolved in a solution of 200 g of malonic acid diethyl ester in 1 l of absolute tetrahydrofurane, whilst excluding water. A solution of 240 g of crude 3-chloro-4-cyclohexyl-benzyl chloride in 400 ml of absolute tetrahydrofurane is added dropwise to this solution whilst stirring and the mixture is boiled for 12 hours under reflux. It is then evaporated to dryness in vacuo. Crude α-(3-chloro-4-cyclohexyl)-malonic acid diethyl ester remains in the evaporation residue and is immediately processed further.

e. A solution of 210 g of potassium hydroxide in 500 ml of water is added to a solution of 450 g of crude α-(3-chloro-4-cyclohexyl)-malonic acid diethyl ester in 1.2 l of ethanol and the mixture is boiled for 12 hours under reflux. It is then evaporated in vacuo to a volume of about 1 l and the evaporation residue is partitioned between 1 l of ether and 1 l of water. The ether phase is twice extracted with 1 l of water at a time and the aqueous phases are twice extracted with 1 l of ether at a time. The water phases are adjusted to pH 2 with concentrated hydrochloric acid whilst cooling with ice and are extracted 3 times with 1 l of chloroform at a time. The chloroform extracts are twice washed with 500 ml of saturated sodium chloride solution at a time, dried over sodium sulphate and evaporated to dryness in vacuo. The crude α-[3-chloro-4-cyclohexyl]-malonic acid remaining in the evaporation residue is immediately processed further.

f. A solution of 265 g of crude α-[3-chloro-4-cyclohexyl]-malonic acid in 700 ml of absolute pyridine is boiled for 1 hour reflux (until the evolution of carbon dioxide ceases). The pyridine is then distilled off in vacuo and the evaporation residue is partitioned between 1 l of ether and 1 l of water. The aqueous phase is twice extracted with 1 l of ether at a time and the ether phases are twice extracted with 1 l of water at a time. The aqueous phases are adjusted to pH 2 with concentrated hydrochloric acid whilst cooling with ice and are extracted three times with 1 l of methylene chloride at a time. The methylene chloride phases are washed until neutral, dried over sodium sulphate and evaporated in vacuo. The crude 3-(3-chloro-4-cyclohexyl-phenyl)-propionic acid contained in the evaporation residue can be recrystallised from methylene chloride/pentane. Melting point 102°–104° C.

g. 1 ml of absolute dimethylformamide and 500 ml of thionyl chloride are added to a solution of 220 g of crude 3-(3-chloro-4-cyclohexyl-phenyl)-propionic acid in 2 l of absolute benzene and the mixture is boiled for 1 hour under reflux, with exclusion of water. It is then evaporated to dryness in vacuo. Crude 3-(3-chloro-4-cyclohexyl-phenyl)propionyl chloride remains in the evaporation residue.

h. A solution of 234 g of crude 3-(3-chloro-4-cyclohexyl-phenyl)-propionyl chloride in 500 ml of absolute carbon disulphide is slowly added dropwise to a suspension of 140 g of finely powdered aluminum chloride in 1 l of absolute carbon disulphide at room temperature, whilst cooling and excluding water. After completion of the addition, the mixture is stirred for a further 10 hours at room temperature. The bulk of the solvent is then distilled off in vacuo at room temperature, the residue is poured onto 1.5 kg of ice and the mixture is extracted three times with 1 l of methylene chloride at a time. The organic extracts are successively washed with 1 l of 2 N hydrochloric acid, water, saturated sodium bicarbonate solution and twice with water, dried over sodium sulphate and evaporated in vacuo. Using pentane, 5-cyclohexyl-6-chloro-1-indanone of melting point 85°–88° C crystallises from the evaporation residue; it is filtered off and dried.

i. 3.6 g. of sodium hydride (60% strength in mineral oil) are added in portions to a suspension of 15 g of 5-cyclohexyl-6-chloro-1-indanone and 31 g of triphenylmethoxymethyl-phosphonium bromide at room temperature, whilst stirring under a nitrogen atmosphere. After completion of the addition (about 60 minutes) the mixture is stirred for a further 2 hours at room temperature and overnight at 80° C. It is then allowed to cool to room temperature and partitioned between 200 ml of methylene chloride and 200 ml of water. The aqueous phase is twice washed with 200 ml of methylene chloride at a time and the organic phases are washed with 200 ml of 1 N hydrochloric acid and 200 ml of water, dried over sodium sulphate and evaporated in vacuo (ultimately at 0.1 mm) at 60° C. The black crystalline residue is extracted repeatedly with ether. The ether extracts are evaporated in vacuo. The crude 1-methoxy-methylidene-5-chloro-6-cyclohexyl-indane obtained in the evaporation residue is purified by chromatography on 200 g of silica gel, with benzene as the eluting agent. The chromatographically pure oily product (cistrans mixture) is directly processed further.

k. 15 ml of 40% strength perchloric acid are added to a solution of 9 g of 1-methoxy-methylidene-5-chloro-6-cyclohexyl-indane in 150 ml of absolute tetrahydrofurane and the mixture is allowed to boil for 90 minutes under reflux. It is then left to cool to room temperature and partitioned between 200 ml of ether and 200 ml of water. The aqueous phase is twice extracted with 200 ml of ether at a time and the organic phases are washed with saturated sodium bicarbonate solution and water, dried over sodium sulphate and evaporated in vacuo. The crude 5-chloro-6-cyclohexyl-indane-1-aldehyde which remains in the evaporation residue is directly processed further.

l. 3.5 g. of hydroxylamine hydrochloride and 3.5 g of sodium acetate are added to a solution of about 8 g of crude 5-chloro-6-cyclohexyl-indane-1-aldehyde in 75 ml of ethanol and the mixture is warmed to 60° C for 15 minutes. It is then treated with water until a homogeneous clear solution is produced and is left to stand for 60 minutes at 60° C. It is cooled to room temperature, 200 ml of water are added and the mixture is extracted three times with 200 ml of methylene chloride at a time. The organic phases are dried over sodium sulphate and evaporated in vacuo. The crude 5-chloro-6-cyclohexyl-indane-1-aldoxime which remains in the evaporation residue is directly processed further.

m. 600 mg of finely powdered potassium hydroxide are added to a suspension of 500 mg of crude 5-chloro-6-cyclohexyl-indane-1-aldoxime in 20 ml of ethylene glycol and the mixture is stirred for 3 hours at 190° C under nitrogen. It is then cooled to room temperature and the reaction mixture is partitioned between 50 ml of ether and 50 ml of water. The aqueous layer is twice washed with 50 ml of ether at a time. The organic phases are extracted with 50 ml of water and the aqueous phases are adjusted to pH 2 with concentrated hydrochloric acid and extracted twice, with 50 ml of methylene chloride at a time. The methylene chloride phases are washed until neutral, dried over sodium sulphate and evaporated to dryness in vacuo. Chromatography of the evaporation residue on 20 g of silica gel, with benzene/ethyl acetate/glacial acetic acid (80:20:1) as the eluting agent, yields pure 5-chloro-6-cyclohexyl-1-indanecarboxylic acid of melting point 140°–143° C (from petroleum ether).

n. Analogously to Example 1a, 5-chloro-6-cyclohexyl-1-indanecarboxylic acid methyl ester is manufactured from 5-chloro-6-cyclohexyl-1-indanecarboxylic acid and is processed further in the crude state.

EXAMPLE 13

6.6 g of chromatographed 1-cyano-5-cycloheptyl-benzocyclobutene in 40 ml of ethanol and 40 ml of 20 percent strength aqueous sodium hydroxide solution are boiled for 7 hours under reflux. The excess ethanol is distilled off in vacuo. The residue is dissolved in approx. 50 ml of water and cold dilute hydrochloric acid is added. The carboxylic acid is extracted with ether-methylene chloride. The solution is extracted three times with 2 N sodium carbonate solution. The sodium carbonate solution is acidified with 2 N hydrochloric acid whilst cooling with ice and the oily 5-cycloheptyl-benzocyclobutene-1-carboxylic acid which precipitates is extracted with methylene chloride. The solution is washed with water, dried over sodium sulphate, filtered and evaporated. The residue crystallises overnight. It is dissolved in 27 ml of 1 N sodium hydroxide solution. The residue which remains after evaporation of this solution is dissolved in hot ethanol and caused to crystallise by means of acetone-ether. The sodium salt of 5-cycloheptyl-1-benzocyclobutenecarboxylic acid is obtained as light yellow crystals of melting point 230°–250° C.

1-Cyano-5-cycloheptyl-benzocyclobutene, used as the starting product, can be manufactured as follows:

a. A mixture of 202 g of p-bromo-acetophenone, 170 g of ethylene glycol, 3.4 g of p-toluenesulphonic acid, 1.7 litres of benzene and 4 drops of concentrated sulphuric acid is boiled for approx. 35 hours under reflux. The water produced during the ketalisation is removed from the reaction mixture by means of a water separator. 3 ml of absolute pyridine are then added to the hot solution and the latter is allowed to cool. 200 ml of saturated sodium carbonate solution are then added to the mixture whilst stirring, and the organic phase is separated off. The latter is again washed with 100 ml of saturated sodium carbonate solution and thereafter with water, dried over sodium sulphate, filtered and evaporated. The crystalline residue, p-bromo-acetophenone-ethylene-ketal of melting point 43°–44° C, can be directly processed further.

b. 25.6 g of magnesium filings are twice washed with chloroform and dried hot in vacuo. A few crystals of iodine are then added and the mixture is heated in vacuo. The magnesium activated in this way is initially introduced into a stirred flask and covered with 350 ml of absolute tetrahydrofurane. This mixture is warmed to approx. 65°–70° C and approx. 50 ml of a solution prepared from 251 g of p-bromoacetophenone-ethylene-ketal and 250 ml of absolute tetrahydrofurane is allowed to run in. The mixture is left until the Grignard reaction starts (approx. 5–10 minutes) and the rest of the ketal solution is then added dropwise in such a way that the internal temperature does not exceed 70° C. Thereafter the reaction mixture is stirred for 1 hour at 65°–70° C, cooled to 20° C and diluted with 520 ml of absolute tetrahydrofurane. 100 g of cycloheptanone are then added dropwise whilst stirring and cooling with ice. In the course thereof, the temperature of the solution should not exceed 30° C. After the addition, the mixture is stirred for a further hour at 30°–40° C. The solvent is now removed in vacuo at 40° C and 800 ml of a saturated ammonium chloride solution and ice are added to the residue. The mixture is then extracted four times with 300 ml of ether at a time. The ether phase is washed once with aqueous ammonium chloride solution and once with sodium carbonate solution, dried over sodium sulphate, filtered and evaporated. The residue, a yellow oil, is distilled at 0.05 mm Hg; in doing so, an oil which can be caused to crystallise from ether-petroleum ether passes over at 160°–79° C. 2-[p(1-Hydroxycycloheptyl)-phenyl]-2-methyl-1,3-dioxolane is thus obtained as white crystals of melting point 77°–79° C.

c. 66.0 g of this product are dissolved in 660 ml of glacial acetic acid and 34 ml of concentrated hydrochloric acid and 66.0 ml of water are added. This mixture is stirred for 1 hour at 60° C internal temperature and then diluted with 1,250 ml of water at room temperature. The reaction mixture is then extracted with ether. The ether phase is repeatedly extracted by shaking with 150 ml of 1 N sodium hydroxide solution at a time, washed with water until neutral, dried over sodium sulphate, filtered and evaporated. The residue, a light brown oil, on distillation yields p-(1-cycloheptenyl)-acetophenone as crystals of melting point 36°–38° C.

d. 45.6 g of distilled p-(1-cycloheptenyl)-acetophenone are hydrogenated in 530 ml of ethyl acetate in the presence of 4.3 g of 5 percent strength palladium on calcium carbonate, in a hydrogen atmosphere under normal pressure. After 11 minutes, 4.76 litres of hydrogen have been taken up; the hydrogenation is then stopped. The catalyst is filtered off and the solution is evaporated. The residue, a colourless oil, is practically pure p-cycloheptyl-acetophenone (boiling point 123° C/0.04 mm Hg) and can be employed, without additional purification, for the following reaction.

e. A mixture of 48.2 g of p-cycloheptyl-acetophenone, 16.2 g of sulphur and 43.5 g of morpholine is boiled for 3 hours at a bath temperature of 130°–140° C. The reaction mixture is then poured into 200 ml of hot absolute alcohol. On standing in ice, p-cycloheptylphenyl-thioacetmorpholide precipitates as brown crystals of melting point 68°–112° C.

f. A mixture of 140 g of the crude morpholide, 280 g of a 50 percent strength aqueous potassium hydroxide solution and 500 ml of ethanol is boiled under reflux for 6 hours. The ethanol is then distilled off in vacuo and the residue is dissolved in water. Animal charcoal is added to this solution, which is then filtered through diatomaceous earth (Celite). The brown filtrate is acidified with concentrated hydrochloric acid whilst cooling with ice. The oil which hereupon separates out is taken up in ether. The ether phase is washed with water until neutral, dried over sodium sulphate, filtered and evaporated. The crystalline residue is taken up in ether and converted into the sodium salt by means of saturated aqueous sodium carbonate solution. The aqueous solution is acidified with concentrated hydrochloric acid whilst cooling with ice. The acid which only partially precipitates as crystals is taken up in ether. The ether solution is washed with water, dried over sodium sulphate, filtered and evaporated. The p-cycloheptylacetic acid which remains slowly crystallises to give a solid product of melting point 74°–86° C.

g. Hydrogen chloride is passed into a solution of 96 g of p-cycloheptyl-phenylacetic acid in 1.5 litres of absolute methanol at 0° C. This solution is left to stand overnight and is then evaporated in vacuo. The residue is taken up in ether. The ether phase is neutralised with aqueous sodium carbonate solution, dried over sodium sulphate, filtered and evaporated. The dark brown oil is distilled in a high vacuum. Hereupon, p-cycloheptyl-phenylacetic acid methyl ester passes over as a colorless oil of boiling point 142°–148° C/0.2 mm Hg.

h. 87.3 g of p-cycloheptyl-phenylacetic acid methyl ester in 600 ml of absolute ether are added dropwise, whilst cooling with ice and stirring, to 13.3 g of lithium aluminium hydride in 1,800 ml of absolute ether. Thereafter the mixture is stirred for 4 hours at room temperature. The reaction mixture is then carefully decomposed with 13.3 ml of water, 13.3 ml of 15 percent strength sodium hydroxide solution and finally with 43 ml of water. The whole is filtered through diatomaceous earth (Celite) and the filtrate is dried over sodium sulphate, filtered and evaporated. The residue, a light yellow oil, is distilled in a high vacuum, whereupon colourless crystalline β-(p-cycloheptyl-phenyl)-ethanol of boiling point 124°–9° C/0.1 mm Hg and melting point 42°–44° C is obtained.

i. 73.6 g of β-(p-cycloheptyl-phenyl)-ethanol are mixed with 31.6 ml of absolute pyridine. 29.5 ml of thionyl chloride are added dropwise to this mixture, whilst cooling with ice. Thereafter, the reaction mixture is slowly heated to 100°–110° C and kept at this temperature for 2 hours. The reaction solution is again cooled to room temperature, 69 ml of water are added, and the whole is extracted with a mixture of ether and chloroform. The organic phase is washed twice with 2 N sodium carbonate solution, three times with 2 N hydrochloric acid and finally once with 2 N sodium carbonate solution, dried over sodium sulphate, filtered and evaporated. The residue, a brown oil, is distilled in a high vacuum. Hereupon, β-(p-cycloheptyl-phenyl)-ethyl chloride is obtained as a light yellow oil of boiling point 130°–5° C/0.2 mm Hg.

j. 18.3 ml of bromine (1 drop/5 seconds) are added dropwise, whilst cooling with water, to a mixture of 69.4 g of β-(p-cycloheptyl-phenyl)-ethyl chloride and 330 mg of iodine. Thereafter the reaction mixture is left to stand overnight at room temperature and is then taken up in ether, and the ether phase is shaken three times with water, three times with 2 N sodium carbonate solution and twice with 5 percent strength sodium thiosulphate solution, dried over sodium sulphate, filtered and evaporated. The light yellow oil which remains consists of a 3:1 mixture of β-(2-bromo- and β-(3-bromo-4-cycloheptyl-phenyl)-ethyl chloride. This mixture requires neither purification nor separation; both isomers lead to the same cyanobenzocyclobutene on cyclisation with sodium amide.

k. A solution of 93.0 g of a mixture of the isomeric β-(bromo-cycloheptyl-phenyl)-ethyl chlorides in 900 ml of dimethylsulphoxide is added dropwise to 59.5 g of powdered sodium cyanide in 600 ml of dimethylsulphoxide at 40° C, whilst stirring. Thereafter, the mixture is stirred for a further 1½ hours at 80° C, allowed to cool to room temperature and treated with 3 litres of ice water. The reaction mixture is then extracted with a mixture of methylene chloride and ether. The organic phase is washed 6 times with water, dried over sodium sulphate, filtered and evaporated. The light brown residue is distilled in a high vacuum. This yields a light yellow oil of boiling point 158°–69° C/0.08 mm Hg which consists of a mixture of the isomeric β-(bromo-cycloheptyl-phenyl)-propionitriles. This mixture can be cyclised without a further purification operation.

l. 17.3 g of distilled isomer mixture of β(2-bromo- and β-(3-bromo-4-cycloheptyl-phenyl)-propionitrile are added dropwise over the course of 2–3 minutes to a solution of potassium amide prepared from 10.9 g of potassium metal in 200 ml of liquid ammonia and 100 mg of iron trinitrate. After 30 minutes, 50 g of solid ammonium chloride are introduced in portions. The ammonia is allowed to evaporate overnight, whilst stirring. 200 ml of water are added to the residue, and the mixture is extracted 3 times with ether. The ether solution is washed five times with water, dried over sodium sulphate and evaporated. The residue, a dark brown oil, is chromatographed on 134 g of silica gel (0.05–0.2 mm, highest purity, Merck AG). The fractions eluted with benzene are practically pure 1-cyano-5-cycloheptyl-benzocyclobutene (light yellow oil).

EXAMPLE 14

A solution of 5 g of 5-cycloheptyl-6-chloro-1-indanecarboxylic acid chloride in 50 ml of absolute tetrahydrofurane is slowly added dropwise, whilst stirring, to a solution of 2.1 g of 2-pyridinemethanol and 3.2 g of triethylamine in 50 ml of absolute tetrahydrofurane at −10° C, under anhydrous conditions. Thereafter, the mixture is stirred for a further 2 hours at room temperature. The precipitate formed is filtered off and the filtrate is partitioned between 3 times 200 ml of ice water and twice 200 ml of ether. The organic phases are successively washed with saturated sodium bicarbonate solution and water, dried over sodium sulphate and evaporated in vacuo. The evaporation residue is filtered through a short column of silica gel (a 10-fold amount), using ether as the eluting agent. The crude oily product thus obtained is dissolved in as little ethanol as possible and the solution is adjusted to pH 3 with alcoholic hydrochloric acid solution and evaporated to dryness. Using ether, 5-cycloheptyl-6-chloro-indane-1-carboxylic acid 2-pyridine-methyl ester hydrochloride of melting point 58°–61° C crystallises after some time.

The starting material can be obtained as follows: A solution of 5 g of 5-cycloheptyl-6-chloro-indane-1-carboxylic acid in 100 ml of absolute benzene and 30 ml of thionyl chloride is boiled for 3 hours under reflux, with exclusion of water. The mixture is then evaporated to dryness in vacuo. The crude 5-cycloheptyl-6-chloro-1-indanecarboxylic acid chloride which has remained in the evaporation residue is processed further without additional purification.

EXAMPLE 15

Analogously to the method described in Example 14, 5-cycloheptyl-6-chloro-1-indanecarboxylic acid 4-pyridinemethyl ester hydrochloride, melting point 158°–162° C (from ethanol-benzene) is obtained starting from 5 g of 5-cycloheptyl-6-chloro-1-indanecarboxylic acid chloride and 40 g of 4-pyridine-methanol.

EXAMPLE 16

A vigorous stream of ammonia gas is passed into a solution of 9 g of 5-cycloheptyl-6-chloro-1-indanecarboxylic acid chloride in 150 ml of absolute benzene at 20° C, for 30 minutes, whilst cooling and stirring. The crude amide which precipitates is filtered off, thoroughly washed with water and dried. Two crystallisations from ethanol yield pure 5-cycloheptyl-6-chloro-1-indanecarboxylic acid amide; melting point 170°–171° C.

EXAMPLE 17

A solution of 9 g of 5-cycloheptyl-6-chloro-1-indanecarboxylic acid chloride in 80 ml of absolute benzene is slowly added dropwise to a solution of 3.2 g of N-methylpiperazine and 3.8 g of triethylamine in 150 ml of absolute benzene at 15° C, whilst stirring in an anhydrous atmosphere. After completion of the addition, the mixture is stirred for a further hour at room temperature. The reaction solution is extracted with twice 200 ml of water and 200 ml of 2 N sodium hydroxide solution. The organic phase is washed with water, dried over sodium sulphate and evaporated to dryness in vacuo. The evaporation residue is dissolved in 150 ml of absolute ethanol and one equivalent of ethanolic hydrochloric acid. 5-Cycloheptyl-6-chloro-1-indanecarboxylic acid 4-methylpiperazide hydrochloride, melting point 264°–250° C, crystallises from the cold solution.

EXAMPLE 18 a. A solution of 6 g of 5-cyclohexyl-6-chloro-1-indanecarboxylic acid methyl ester, 0.9 g of paraformaldehyde and 0.7 ml of benzyl-trimethylammonium methoxide (40% strength in methanol) in 20 ml of dimethylsulphoxide is stirred for 4 hours at 80° C. It is then cooled to room temperature, neutralised with glacial acetic acid and evaporated in vacuo to a volume of about 10 ml. The evaporation residue is partitioned between 50 ml of ether and 50 ml of ice water and the aqueous solution is extracted twice more with 50 ml of ether at a time. The organic phases are washed three times with 50 ml of 1 N sodium carbonate solution at a time, 50 ml of 2 N acetic acid and twice with 50 ml of water at a time, whilst cooling with ice, and are dried over sodium sulphate and evaporated in vacuo. The oily 1-hydroxymethyl-5-cyclohexyl-6-chloro-1-indanecarboxylic acid methyl ester which remains in the residue is processed further without additional purification.

b. 30 ml of 2 N sodium hydroxide solution are added to a solution of 6.5 g of crude 1-hydroxymethyl-5-cyclohexyl-6-chloro-1-indanecarboxylic acid methyl ester in 200 ml of ethanol. After a short time, a solid begins to separate out from the reaction solution. The mixture is left to stand for 2 hours at room temperature. It is then filtered and the filter residue is thoroughly washed with ethanol and ether. The sodium salt of 1-hydroxymethyl-5-cyclohexyl-6-chloro-1-indanecarboxylic acid thus obtained is partitioned between 50 ml of ether and 50 ml of 1 N hydrochloric acid. The hydrochloric acid solution is extracted twice with 50 ml of ether at a time and the organic phases are washed until neutral, dried over sodium sulphate and evaporated in vacuo. The evaporation residue, on recrystallisation from ether-hexane, yields 1-hydroxymethyl-5-cyclohexyl-6-chloro-1-indanecarboxylic acid; melting point 195°–197° C.

We claim:
1. An analgesic or antiinflammatory pharmaceutical composition comprising an analgesically or antiinflammatory effective amount of a compound corresponding to the formula

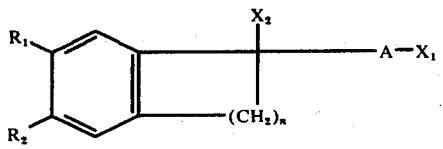

wherein A denotes the direct bond or a methylene group, one of the groups $R_1$ and $R_2$ denotes hydrogen, halogen, alkyl with 1 to 4 carbon atoms, or trifluoromethyl and the other denotes cycloalkyl with 4 to 8 carbon atoms, $X_1$ and $X_2$ independently of one another denote a carboxyl group or an alkoxycarbonyl group with 2 to 5 carbon atoms, and n denotes an integer from 1 to 3, or a pharmaceutically acceptable salt thereof, together with a pharmaceutical carrier.

2. A composition according to claim 1, wherein the effective compound is 1-carboxy-5-cyclohexyl-1-indaneacetic acid its monomethyl or methyl, ethyl ester or pharmaceutically acceptable salts thereof.

3. A composition according to claim 1, wherein the effective compound is 1-methoxycarbonyl-5-cyclohexyl-6-chloro-1-indanecarboxylic acid, or a pharmaceutically acceptable salt thereof.

4. A composition according to claim 1, wherein the effective compound is 1-butoxycarbonyl-5-cyclohexyl-6-chloro-1-indanecarboxylic acid, or a pharmaceutically acceptable salt thereof.

5. A composition according to claim 1, wherein the effective compound is 1-methoxycarbonyl-5-cycloheptyl-6-chloro-1-indanecarboxylic acid, or a pharmaceutically acceptable salt thereof.

6. A composition according to claim 1, wherein the effective compound is 1-propoxycarbonyl-5-cycloheptyl-6-chloro-1-indanecarboxylic acid, or a pharmaceutically acceptable salt thereof.

7. A composition according to claim 1, wherein the effective compound is 1-butoxycarbonyl-5-cycloheptyl-6-chloro-1-indanecarboxylic acid, or a pharmaceutically acceptable salt thereof.

8. The method for treating inflammatory conditions in a mammal suffering therefrom, which comprises administering to said mammal an antiinflammatory effective dose of a composition according to claim 1.

* * * * *